United States Patent [19]
Xu et al.

[11] Patent Number: 5,543,298
[45] Date of Patent: Aug. 6, 1996

[54] METHOD FOR ASSAYING THE SOD ACTIVITY BY USING A SELF-OXIDIZABLE COMPOUND NECESSARY FOR ITS IMPLEMENTATION, SELF-OXIDIZABLE COMPOUNDS AND PREPARATION THEREOF

[75] Inventors: Jinzhu Xu, Ivry sur Seine; Jean-Claude Y. Yadan, Paris; Marc E. Moutet, Bagneux; Jean R. Chaudiere, Saint Maur des Fosses, all of France

[73] Assignee: Oxis International S.A., Bonneuil-sur-Marne, France

[21] Appl. No.: 244,866

[22] PCT Filed: Nov. 25, 1992

[86] PCT No.: PCT/FR92/01093

§ 371 Date: Jun. 6, 1994

§ 102(e) Date: Jun. 6, 1994

[87] PCT Pub. No.: WO93/11258

PCT Pub. Date: Jun. 10, 1993

[30] Foreign Application Priority Data

Nov. 29, 1991 [FR] France .................... 91 14781
Feb. 24, 1992 [FR] France .................... 92 02082

[51] Int. Cl.$^6$ .............. C12Q 1/26; C12Q 1/00; G01N 33/48; C07H 1/00
[52] U.S. Cl. .................. 435/25; 435/4; 435/810; 435/975; 435/189; 435/28; 435/26; 436/63; 536/1.11; 560/117; 540/520; 540/521; 514/1; 514/23; 514/740; 514/753
[58] Field of Search .................... 435/25, 4, 28, 435/133, 189, 26, 14, 810, 975; 424/94.4; 436/63; 536/1.11; 560/117; 540/520; 514/1, 23, 740, 753

[56] References Cited

U.S. PATENT DOCUMENTS

| | | | |
|---|---|---|---|
| 3,558,435 | 1/1971 | Rey et al. .................... | 435/25 |
| 4,279,993 | 7/1981 | Magers et al. ................ | 435/25 |
| 4,569,766 | 2/1986 | Kool et al. ................... | 435/25 |
| 4,629,696 | 12/1986 | Elstner ....................... | 435/25 |
| 4,673,635 | 6/1987 | Yamanishi et al. ............ | 435/25 |
| 4,716,110 | 12/1987 | Wada et al. .................. | 435/25 |
| 4,801,538 | 1/1989 | Hanada et al. ................ | 435/25 |
| 5,094,943 | 3/1992 | Siedel et al. ................. | 435/25 |

FOREIGN PATENT DOCUMENTS

2065302 6/1981 United Kingdom.
8605689 9/1986 WIPO.

OTHER PUBLICATIONS

Martin et al, "Archives of Biochem & Biophysics", vol. 255, No. 2, pp. 329–336, Jun. 1987.

Misra et al, "Jour of Biological Chem", vol. 247, No. 10, pp. 3170–3175, May 1972.

Primary Examiner—John Kight, III
Assistant Examiner—Louise N. Leary
Attorney, Agent, or Firm—Jacobson, Price, Holman & Stern, PLLC

[57] ABSTRACT

The method for assaying the SOD (super oxide dismutase) activity in liquid medium is based on the activation of self-oxidization, by SOD activity, of a reactive agent having the general formula (I) wherein either n is 1 or 2, $R^1$ is —$OR^4$ or —$NR^5R^6$; $R^2$ is H, —$OR^4$, alkyl (1–6C), —$CH_2$— or —$CH_2$—$CH_2$—, to form a ring by binding to the phenyl substituent, at meta with respect to $R^1$; and $R^3$ is H, alkyl (1–6C) or —$OR^4$ (if $R^2$ is different from —$OR^4$); with $R^4$ being H or alkyl (1–6C); $R^5$ being H, alkyl (1–6C), —$CH_2COOH$, —$C_6H_5COOH$ or —$C_6H_5SO_3H$; and $R^6$ is H, alkyl (1–6C) or —$CH_2COOH$; or n is 1, $R^1$ is —$OR^4$, $R^2$ is —$CH_2$—O—, in order to form a ring by bonding of O with the phenyl substituent, at meta with respect to $R^1$; and $R^3$ is H or —$OR^4$. Application to assaying the SOD activity in a sample, specially a biological sample, particularly by a single measurement and one calibrating curve.

18 Claims, 7 Drawing Sheets

METHOD FOR ASSAYING THE SOD ACTIVITY BY USING A SELF-OXIDIZABLE COMPOUND NECESSARY FOR ITS IMPLEMENTATION, SELF-OXIDIZABLE COMPOUNDS AND PREPARATION THEREOF

The present invention relates to the assaying of superoxide dismutase (SOD) activity.

It relates more particularly to a new process for the assay of SOD activity, especially in biological samples, using auto-oxidizable compounds which are defined below, to kits for the implementation of this process and to new compounds which can be used in this process, and to their preparation.

The tissues of aerobic organisms, and those of the human organism in particular, are the site of continual production of superoxide ion $O_2.^-$, which results from the process of cell respiration and from numerous essential metabolic pathways.

This production of superoxide ion increases considerably when these organisms are subjected to an "oxidizing stress" of toxicological origin (hyperoxia, irradiation, intoxication by xenobiotics which generate free radicals, in particular) or of physiopathological origin (inflammation, ischaemia, post-ischaemic reperfusion, in particular).

It is accepted by the entire scientific community that the superoxide ion is highly toxic, although the mechanisms underlying this toxicity remain the subject of controversy (reference 1).

In order to protect themselves against the harmful effects of the superoxide ion, aerobic organisms possess enzymatic systems, the superoxide dismutases (SODs), which catalyse the breakdown of the superoxide ion in accordance with the following dismutation reaction:

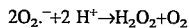

$$2O_2.^- + 2 H^+ \rightarrow H_2O_2 + O_2$$

Because of the major protective role of this dismutation reaction with regard to the toxicity of the superoxide ion, the catalytic activity of intra- and extra-cellular SODs determines the survival of the tissues of an aerobic organism (references 2 to 5).

The assay of SOD activity is therefore of prime interest to biological researchers and to laboratories of clinical chemistry, on condition that it should be possible to carry it out using a method which is sensitive, specific, rapid and relatively simple.

Numerous methods for assaying SOD activity have been published and commented on (references 6 to 10), but it is generally accepted that there does not yet exist a satisfactory compromise between reliability and complexity in the existing methods, since the measurement of SOD activity poses two major problems which none of the methods published to date has been able to resolve in a simple fashion.

The first problem is that of the spontaneous decomposition of the sole substrate, the superoxide ion, which is very rapid at a pH of about 7 and which, although highly decelerated, remains significant at a pH of 9, the pH above which certain types of natural SODs are rapidly deactivated. To obtain a stationary concentration which is sufficiently stable therefore requires the presence of a dynamic source of superoxide ion in the assay solution.

Electrolytic sources require complex equipment and a prior extraction of the SOD catalyst, which is prohibitive in clinical chemistry.

Photochemical sources, such as riboflavin, lead to methods which cannot be standardized and which are complex to carry out.

Enzymatic sources, such as xanthine oxidase, require solutions to be prepared at the time of use. They are expensive, a source of artifacts, and are difficult to automate.

Purely chemical sources come down to auto-oxidizable compounds such as 6-hydroxydopamine, pyrogallol, hydroxylamine or the sulfite ion, whose autoxidation is generally inhibited by SOD.

These chemical reagents rarely give results which are precise and sensitive on crude biological extracts, and they require the extemporaneous preparation of an anaerobic solution of the reagent; their use is therefore difficult to automate.

The second problem is related to the fact that it is difficult to measure directly ("direct" assay) the disappearance of the superoxide substrate $O_2.^-$ as a function of time, or the appearance of its dismutation products, hydrogen peroxide $H_2O_2$ and oxygen, because of the concentrations and the pH values which are accessible under the conditions of an assay of SOD activity.

The only "direct" spectrophotometric method is that of MARKLUND (references 11 and 12), which measures the rate of disappearance of the superoxide ion at pH 9.5, which does not permit the assay of all natural SODs.

This method requires a rapid spectrophotometer. The high concentrations of superoxide ion and the wavelength (250 nm) which are used make the method relatively imprecise, which obliges the experimenter to carry out a number of measurements in order to obtain an average value. In addition, it is necessary to add catalase to avoid the deactivation of the SOD-Cu/Zn, and it is necessary to reprepare a new solution of potassium superoxide immediately before each assay.

This direct spectrophotometric method is therefore complicated to carry out, and it does not appear possible to improve it in any significant way.

The corollary of this is that the popular methods, in other words those which are used most often, are generally indirect: they rest on the competition between the SOD activity which it is attempted to measure and the reaction of the superoxide ion with a chromogenic scavenger such as ferrocytochrome C or nitro blue tetrazolium (NBT), the reaction product of which can be measured by UV/visible spectrophotometry. A chemiluminescent scavenger, such as luminol or lucigenin, may also be used with a greater sensitivity of the measurement, but the problems of interferences and of instrumental availability preclude the use of such methods by a non-specialist laboratory.

In addition to the often inadequate specificity of the chromogenic reagents with regard to the superoxide ion, the principal disadvantage of the competitive assays is that they require a linearization of the inhibition (by SOD) values, over 5 or 6 samplings of increasing dilutions.

Finally, a certain number of immunoassays of SOD-Cu/Zn or of SOD-Mn are known.

Some of them are very sensitive, but they give no information on the enzymatic activity of the sample, which depends in particular on the degree of possible deactivation of the enzyme. Moreover, they take a long time to carry out and are relatively complex.

Artifacts of measurements and demultiplication of the assay are therefore intrinsically linked to all the spectrophotometric methods which are accessible to the majority of laboratories, which does not satisfy the requirements of research laboratories and remains incompatible with the imperatives of standardization in clinical chemistry.

If use is made of UV/visible spectrophotometry, it seems difficult—or even impossible—to develop a method of assay which is at one and the same time sensitive, more specific, more simple and more reliable than the existing methods, unless recourse is had to the monitoring of the kinetics of a reaction which is activated by SOD activity rather than to that of a reaction which is inhibited by SOD activity or to a "direct" method.

In this respect, a recent method (references 13 and 14), which uses an auto-oxidizable colourant, haematoxylin, differs from others in the measurement, for which it utilizes activation of the autoxidation of the reagent by SOD activity.

In effect, haematoxylin undergoes autoxidation at a pH>6.5 (reference 13). The rate of autoxidation factor of close to 100 between pH 7 and 9. SOD inhibits this autoxidation at a pH<8.1, while activating it at a pH>8.1. This observation led to the development of an assay, based on the spectrophotometric monitoring of the formation of haematein at 560 nm, which is accelerated by SOD at alkaline pH. The application of this method is complex because of the instability of the reagent, and it remains dependent on a phase of preparation of the sample (dialysis) in order to remove the interferences which are due to the presence of reducing compounds such as, for example, glutathione.

Moreover, the low sensitivity of the assay (at a pH>8.1), linked in part to the decomposition of the measured oxidation product, haematein, but also to the presence of two sites of potential oxidation (catechols), limit the interest and the exploitation of this method.

In conclusion, the haematoxylin method, although having a certain interest, possesses some invalidating disadvantages which do not allow it to be used in general for assaying SOD activity, in particular in biological samples.

The objectives of the present invention are, in particular:

to make available a reagent whose autoxidation product is stable during measurement;

to increase the sensitivity of the assay in relation to a method using haematoxylin (under conditions in which autoxidation is activated);

to enable the elimination of the most likely possible interferences, such as those linked to the presence of mercaptans such as glutathione, for example;

to develop a process which uses a reaction medium with a pH of less than or equal to 9, so as to permit an assay of the activity of known SODs without the risk of rapid deactivation.

These objectives are attained in accordance with the invention, which utilizes the chemical reagents defined below, which have the property of undergoing autoxidation in an oxygenated solution, to autoxidation in an oxygenated solution, to lead to a chromophoric product, the kinetics of whose appearance is increased in the presence of a catalyst of the SOD type.

The structure of these reagents is characterized, in particular, by an aromatic ring with a catechol function, which is linked via a tertiary benzyl carbon to an aromatic ring which is substituted with an electron-donating group.

The autoxidation product of these reagents has an absorption wavelength which is very different from that characterizing the reagent itself.

The invention therefore provides a process which employs these reagents, which enables the SOD activity of any catalyst to be assayed in aqueous medium, using a single UV/visible absorption measurement, which process is markedly more simple in its application than that of the other spectrophotometric methods which have been described beforehand.

The invention also provides a process for the stabilization of a stock solution of the chemical reagents defined below, by means of boron derivatives, in particular boric acid and its derivatives such as phenyl-boric acid.

The invention furthermore provides a process for assaying the SOD activity of the type described above, in the presence of mercaptans, by virtue of the use of a rapid reagent for thiol groups, which enables the elimination of the corresponding interferences, in particular those which are caused by the presence of glutathione or albumin in the sample.

According to one of its aspects, the subject of the invention is a process for the assay of superoxide dismutase (SOD) activity in a liquid medium, which process utilizes activation of the autoxidation of a reagent by SOD activity, characterized in that the said reagent is a compound conforming to the general formula (I):

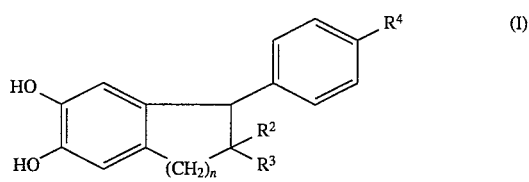

in which:
either:

n=1 or 2, $R^1$=—$OR^4$ or —$NR^5R^6$, $R^2$=hydrogen, —$OR^4$ alkyl (with 1 to 6 carbon atoms) or else —$CH_2$— or —$CH_2$—$CH_2$—, to form a ring by linking with the phenyl substituent, in the meta position in relation to $R^1$, and $R^3$=hydrogen, alkyl (with 1 to 6 carbon atoms) or —$OR^4$ (with the proviso that $R^2$ is different from —$OR^4$), where $R^4$=hydrogen or alkyl (with 1 to 6 carbon atoms), $R^5$=hydrogen, alkyl (with 1 to 6 carbon atoms), —$CH_2COOH$, —$C_6H_5COOH$ or —$C_6H_5SO_3H$, and $R^6$=hydrogen, alkyl (with 1 to 6 carbon atoms) or —$CH_2COOH$;

or:

n=1, $R^1$=—$OR^4$ ($R^4$ being defined as above), $R^2$=—$CH_2$—O—, to form a ring by linkage of the oxygen atom with the phenyl substituent, in the meta position in relation to $R^1$, and $R^3$=hydrogen or —$OR^4$ ($R^4$ being defined as above).

The compound of general formula (I) above in which n=1, $R^1$=—OH, $R^2$=—$CH_2$—O— and $R^3$=—OH is brazilin which is a commercial product.

The other compounds conforming to the general formula (I) defined above may be prepared according to the general procedures which are described hereinafter, generally from commercial products.

However, the compounds in which $R^5$ represents —$C_6H_5COOH$ or —$C_6H_5SO_3H$ are obtained from the synthon of the para-bromophenylaminophenyl type, substituted in an appropriate manner. This synthon is prepared according to the following general procedure.

para-Nitrophenol is alkylated by means of an ester of chloroacetic acid. The derivative obtained is hydrolyzed and then amidated with para-bromoaniline. The corresponding amide is subjected to the reaction of Smiles (reference 15) to give the corresponding diphenylamine derivative. The latter is reduced, diazotized, and substituted in an appropriate manner to give the desired synthon.

General procedure for the synthesis of compounds of series I (n=1 or 2, $R^1$=—$OR^4$ or $NR^5R^6$, $R^2$=hydrogen or alkyl and $R^3$=hydrogen or alkyl):

5,6-Dihydroxindan-1-one or 6,7-dihydroxy-1-tetralone (prepared from veratrole), suitably protected by an alkyl or aralkyl group such as, for example, the methyl or benzyl group, or by a group of silyl type such as, for example, the tert-butyldimethylsilyl group, is treated, either directly or after prior mono- or bis-alkylation (of the α position of the ketone function) using an alkylating agent such as methyl iodide, for example, by the organomagnesian reagent corresponding to phenyl bromide substituted in the para position by an oxygen-containing group such as, for example, the methoxy group, or a nitrogen-containing group such as, for example, the dimethylamino group.

The intermediates thus obtained are reduced and then deprotected to give the compounds of series I.

The following reaction scheme illustrates this procedure.

These compounds are obtained by hydration of the alkenes which are intermediates in the synthesis of compounds of series I, after hydroboration and oxidation; the alcohols thus obtained are then, if appropriate, alkylated with an alkyl halide such as, for example, methyl iodide and then deprotected.

The following reaction scheme illustrates this procedure.

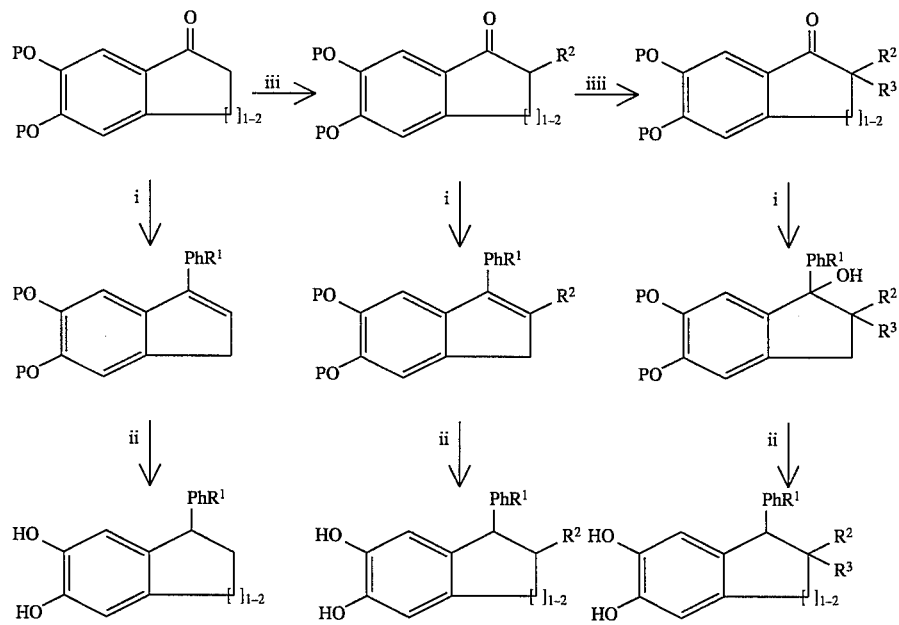

i: $R^1PhMgBr$ ($R^1$ in para position)
ii: reduction then deprotection

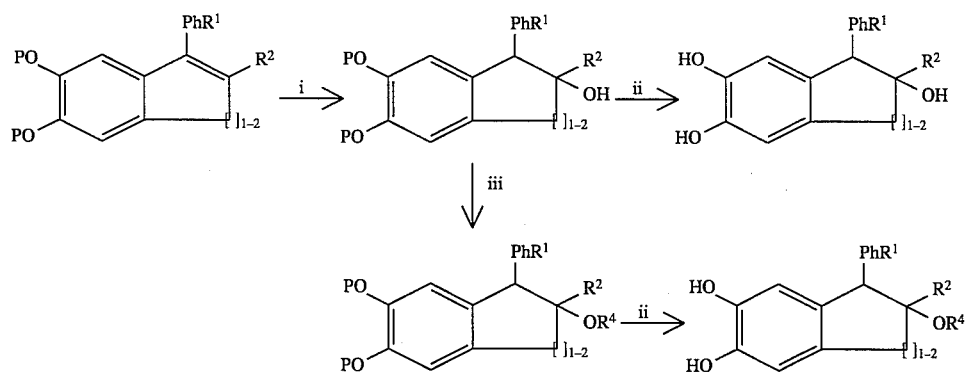

iii: base, $R^2X$
iiii: base, $R^3X$
P: protecting group
General procedure for the synthesis of compounds of series II (n=1 or 2, $R^1$=—$OR^4$ or —$NR^5R^6$, $R^2$=hydrogen or alkyl and $R^3$=—$OR^4$).

i: 1) $BH_3$; 2) $H_2O_2$, NaOH
ii: deprotection
iii: base, $R^4X$
P: protecting group
General procedure for the synthesis of compounds of series III (n=1 or 2, $R^1$=—$OR^4$ or —$NR^5R^6$ and $R^2$=—$CH_2$— or —$CH_2$—$CH_2$— forming a ring by linkage with the phenyl substituent, in the meta position in relation to $R^1$):

To synthesize these compounds, the product of crotonization between 3,4-dihydroxybenzaldehyde, protected in a suitable fashion, and 1-tetralone or 1-indanone which are suitably substituted, is reduced, either directly or indirectly (after preparation of the superior homologue by way of a cyclopropane derivative), by catalytic hydrogenation to give the corresponding saturated derivative. The latter is cyclized in the presence of polyphosphoric acid and the alkene thus obtained is reduced and then deprotected to give the desired compound of series III.

The following reaction scheme illustrates this procedure.

iii: polyphosphoric acid iiii: reduction iiiii: deprotection

P: protecting group

General procedure for the synthesis of compounds of series IV (n=1, $R^1$=—OH, $R^2$=—$CH_2$—O—, to form a ring by linkage of the oxygen atom with the phenyl substituent, in the meta position in relation to $R^1$ and $R^3$=hydrogen or —$OR^4$):

These compounds can be synthesized from brazilin according to the following reaction scheme:

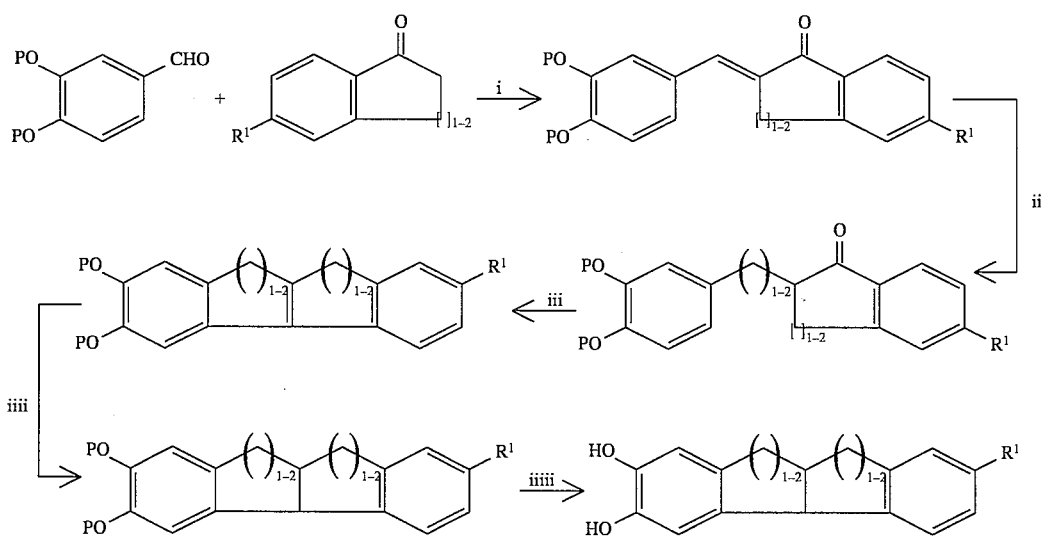

i: $H^+$ ii: reduction (or preparation of the superior homologue then reduction)

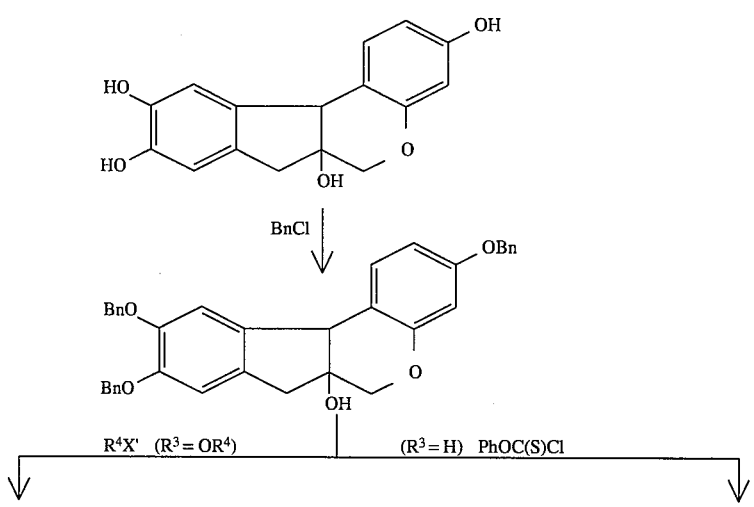

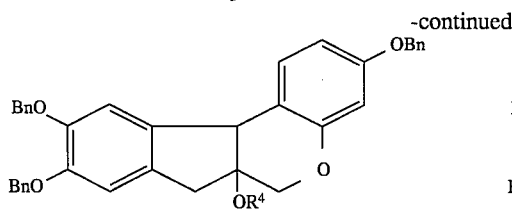

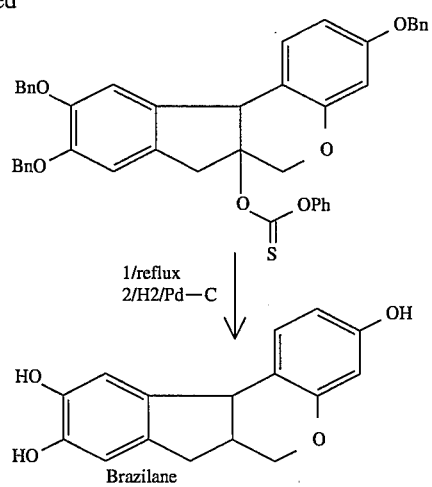

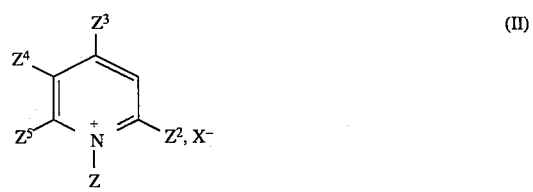

Brazilane

In this scheme:

Bn represents a protecting group of the phenolic OH groups, such as the benzyl group, R⁴ X' represents an alkylating agent.

After having protected the 3 phenolic hydroxyls in the form, for example, of benzyl ether, the tertiary alcohol group is eliminated in the form of phenyl thiono carbonate, for example, or else alkylated using, for example, methyl iodide. The desired product is obtained, after deprotection, by catalytic hydrogenation in the presence, in particular, of palladium on carbon, which is concomitant with a reduction in the case of brazilane.

Examples 9 and 10 of the experimental section which follows illustrate the preparation of compounds of this type. General procedure for the synthesis of compounds of series V (n=1, R¹=—O—alkyl, R²=—CH₂—O—, to form a cycle by linkage of the oxygen atom with the phenyl substituent, in the meta position in relation to R¹ and R³=hydrogen or —OR⁴):

Brazilin or one of its derivatives in which R¹=OH and R³ is different from OH is protected on its two catecholic hydroxyls by a methylene bridge, for example by means of formaldehyde. The derivative obtained is alkylated on its unprotected hydroxyl by means of an alkylating agent such as, for example, an alkyl halide and then deprotected in acid medium.

Example 11 of the experimental section which follows illustrates the preparation of a compound of this type, in which R¹=—O-methyl and R³=—OR⁴ where R⁴=hydrogen.

All of the brazilin derivatives of series IV and V are obtained by chemical modification of its hydroxyl groups. The modifications which are carried out make it possible to modulate the sensitivity of the assay of SOD activity.

When the assay of SOD activity has to be carried out in a medium containing one or more compounds which comprise one or more thiol groups, such as, in particular, a biological medium, the reducing power of the latter groups is capable of causing interferences which it is appropriate to remove.

Such interferences may easily be avoided by adding, to the medium in which the assay is carried out, at least one reagent chosen from compounds of the pyridinium and quinolinium types, whose use as "mercaptan scavengers" is the subject of the French Patent Application filed on 29 Nov. 1991 in the name of BIOXYTECH under the No. 9114782, and whose title is: "Mercaptan-scavenging reagents, their preparation and their applications".

These reagents correspond to the following criteria:

specificity for mercaptans under the operating conditions used, rapidity of reaction, non-interference with the other reagents used in the assay of SOD activity.

More precisely, according to another of its aspects, the invention relates to a process for the assay of superoxide dismutase (SOD) activity in a liquid medium containing one or more mercaptan(s), especially a biological medium, which process utilizes activation of the autoxidation of a reagent by SOD activity, characterized in that the said reagent is a compound conforming to the general formula I defined above and in that the medium additionally contains a quantity, which is capable of totally scavenging the said mercaptans by S-alkylation, of at least one compound conforming to the general formula II:

$$\begin{array}{c} Z^3 \\ Z^4 \diagdown \\ | \\ Z^5 \diagup N^+ \diagdown Z^2, X^- \\ | \\ Z^1 \end{array} \quad (II)$$

in which:

Z¹=alkyl (with 1 to 6 carbon atoms), benzyl, p-nitrobenzyl, phenyl, o,p-dinitrophenyl, —CH₂—COOH or —CH₂—CH₂—COOH;

Z⁴=hydrogen and

Z⁵=hydrogen or alkyl (with 1 to 6 carbon atoms), or

Z⁴ and Z⁵ form, together with the two intermediate carbon atoms, a phenyl ring;

X=halide, sulphonate, fluorosulphonate, phosphonate, tetrafluoroborate or tosylate; and either Z²=vinyl, and Z³=hydrogen or alkyl (with 1 to 6 carbon atoms) (2-vinyl compounds), or Z³=vinyl, and Z²=hydrogen or alkyl (with 1 to 6 carbon atoms) (4-vinyl compounds).

A sulphonate is understood to be an anion of general formula R—SO₃⁻ in which R represents, for example, trifluoromethyl.

Some of these compounds are known, or they can be synthesized by analogy with processes used for the synthesis of known compounds.

The 2-vinyl compounds may thus be synthesized as follows.

The initial derivative (substituted quinoline or pyridine) is subjected to the method of Comins (reference 16), using vinylmagnesium bromide. The compound thus obtained is oxidized with, for example, tetrachloro-1,4-benzoquinone (parachloranil) or sulphur $S_8$. The alkylation of the heterocyclic nitrogen is carried out using an alkylating agent, for example trimethyloxonium tetrafluoroborate, methyl sulfate, benzyl bromide, fluorodinitrobenzene, sodium iodoacetate or sodium 3-bromopyruvate, which are chosen according to the meaning of $Z^1$.

Example 12 of the experimental section which follows illustrates the preparation of a compound of this type.

Moreover, the 4-vinyl compounds can be synthesized as follows.

The corresponding heterocyclic aldehyde (aldehyde function, —CHO, in position 4) is subjected to the Wittig reaction with, for example, triphenylmethylphosphonium bromide, or to the Peterson reaction with, for example, chloromethyltrimethylsilane. The alkylation of the heterocyclic nitrogen is carried out using an alkylating agent, for example trimethyloxonium tetrafluoroborate, methyl sulphate, benzyl bromide, fluorodinitrobenzene, sodium iodoacetate or sodium 4-bromopyruvate, which are chosen according to the meaning of $Z^1$.

Example 13 of the experimental section which follows illustrates the preparation of a compound of this type.

The process according to the invention, especially when it employs at least one "mercaptan scavenger" as defined above, makes it possible to assay the SOD activity of any catalyst in aqueous medium, using a single measurement of the UV/visible absorption, which is markedly more simple to carry out than the spectrophotometric methods described beforehand.

This new assay process thus constitutes a tool of choice for biological research in general and in clinical chemistry, in particular for the development of assay kits.

In the latter case, this assay is capable of providing useful medical information in physiopathological conditions such as diseases of inflammatory or ischemic origin, states of shock, infectious states, systemic diseases and autoimmune diseases, tumours, states of malnutrition, diseases associated with aging, degenerative disorders, haemolytic anaemias and the syndromes of intoxication by environmental pollutants or by medicaments.

The human samples on which this method can be utilized are, in particular, erythrocytes, blood plasma, platelets, leucocytes, synovial fluid, cerebrospinal fluid, urine or any tissue extract.

Moreover, this assay method can be used to carry out the pharmacokinetic studies which are necessary for the development and use of new medicaments which have SOD activity.

This assay method can also be used for the quality control of cosmetic or pharmaceutical preparations which have SOD activity.

In a general manner, this assay method can be used by researchers on any biological sample or any artificial solution which is liable to have SOD activity.

According to a preferred embodiment, the process for the assay of the superoxide dismutase activity of a sample, especially a biological sample, resides in a spectrophotometric measurement of the rate of autoxidation of a compound of general formula I above, in the absence and in the presence of the said sample.

More precisely, according to a preferred embodiment, the invention relates to a process for the assay of superoxide dismutase (SOD) activity in a liquid sample, characterized in that it essentially comprises the steps consisting in:
1) determining the maximum rate of autoxidation Vs of a compound of general formula I in the presence of the sample, by means of the change in the absorbance as a function of time, at the wavelength which characterizes the appearance of the autoxidation product of the compound of general formula I used, in a reaction medium which is buffered to a pH value of from 8.0 to 9.0, triggering the reaction by the addition of an aliquot of a stock solution of the compound of general formula I;
2) determining, under the same conditions, the maximum autoxidation rate $V_c$ of the same compound in the absence of the sample; and
3) determining the SOD activity of the sample by means of the rates $V_s$ and $V_c$ obtained and of a calibration curve established under the same operating conditions.

The reaction medium consists advantageously of an amine buffer such as, for example, 2-amino-2-methyl-1,3-propanediol (AMPD) containing diethylenetriaminepentaacetic acid (DTPA), 0.1 mM, and allowing the pH to be fixed at a value in the range from 8.0 to 9.0 at the measurement temperature, for example by adding sodium hydroxide solution or hydrochloric acid according to the nature of the buffer under consideration.

This reaction medium must be equilibrated at the working temperature and saturated with air at this temperature.

The working temperature chosen, for example 37° C., must be maintained constant during the measurements.

The reaction is triggered by the addition to the reaction medium (with or without SOD) of an aliquot of a stock solution of one of the compounds of general formula I in an aqueous solution or in a water-miscible organic solvent such as, for example, acetonitrile, dimethylformamide or dimethyl sulfoxide, or else in a mixture of such an organic solvent with distilled water.

In order to avoid an extemporaneous preparation of this stock solution or an anaerobic preparation of the latter, the stock solution can be prepared in the presence of a boron derivative such as, for example, boric acid which enables a reagent solution to be obtained which is stable for a period which depends on the respective concentrations of the reagent and the boron derivative, on the respective nature of the reagent and of this derivative and on the storage conditions of the stock reagent solution. Thus a solution of the reagent BXT01050 described below (Example 7), prepared in a 50:50 (volume/volume) mixture of dimethyl sulfoxide/ distilled water and containing boric acid, such that the ratio of the concentrations of boric acid and of reagent are equal to 150, is stable for at least one month if the solution is stored at between 0° and 8° C.

After homogenization of the solution, the change in the absorbance is recorded as a function of time at the wavelength which characterizes the appearance of the autoxidation product of the reagent used (for example 525 nm for the reagent BXT01050 and 539 nm for brazilin), in order to determine the maximum rate of autoxidation.

The determination of SOD activity in a biological sample can be carried out by determining the ratio or the difference of the rates measured in the presence ($V_s$) and in the absence ($V_c$) of the sample.

This ratio or this difference can be recorded, for example, on the ordinate of a calibration curve which has been established under the same operating conditions using, for example, a SOD standard.

This calibration curve can be curveted by representing, as a function of the concentration of the standard used, the variation in the ratio or in the difference of the autoxidation rates measured in the presence ($V_s$) and in the absence ($V_c$) of this standard.

The ratio $V_s/V_c$ varies with the concentration of SOD according to a hyperbolic function of the type $y=1+x/(ax+b)$, in which x represents the concentration of SOD and a and b are constants. The inverse of the difference in the rates as a function of the inverse of the concentration of SOD is one of the possible linearizations of this function.

According to the intensity of the SOD activity to be measured, the sensitivity of the assay in the pH range used (8.0 to 9.0) can be adapted by modifying, for example, one or more of the following parameters: concentration of the compound of general formula I chosen, concentration of the buffer and measurement temperature.

The rate of autoxidation of the reagent used may be modulated also by varying the concentration of boron derivative in the reaction medium.

The existence in a sample, especially a biological sample, of compounds which interfere with the assay is most often evident in a decrease in the rate measured in the presence of the sample in relation to that measured in its absence.

In the case of interferences which are linked to the presence of mercaptans such as, for example, glutathione, the introduction into the reaction medium of a "mercaptan-scavenging reagent" as defined above is then necessary.

Thus 1,4,6-trimethyl-2-vinylpyridinium tetrafluoroborate (compound of Example 12), for example, will be incorporated in a concentration which is fifty times greater than that of glutathione for the assay of SOD activity in an erythrocyte lysate.

If the existence is suspected in a sample, especially a biological sample, of a compound which is liable to introduce an artifactual activation of the autoxidation of the compound of general formula I, or chromogenic compound, a combination such as that described below may be undertaken, which involves making a second measurement carried out under conditions in which the autoxidation is inhibited.

Likewise, in the case of the examination of media, especially biological media, which have a low SOD activity, the sensitivity and the precision of the assay can be increased by combining, with the measure made under conditions of activation of the autoxidation, a measurement carried out under conditions in which the autoxidation is inhibited.

Therefore the invention likewise relates to a process of the type described above, characterized in that it also comprises a measurement carried out under conditions in which the autoxidation is inhibited.

The reaction medium used for this second measurement differs from the medium described above by the use of a buffer at a pH within the range from 7.2 to 7.8, especially a phosphate buffer consisting, for example, of a suitable mixture of potassium dihydrogen phosphate and dipotassium hydrogen phosphate, all other things being equal.

Under these operating conditions the maximum autoxidation rate of the compound of general formula I used is measured in the absence ($V'_c$) and in the presence ($V'_s$) of the sample. The determination of the SOD activity in the sample is then obtained by means of ($V_s-V_c-V'_s+V'_c$).

As previously, the value obtained can be recorded on the ordinate of a calibration curve which has been established under the same experimental conditions and which gives the variation of ($V_s-V_c-V'_s+V'_c$) as a function of the concentration of the standard used.

The new assay method according to the invention which uses as reagent a compound of general formula I is, on the basis of its principle, a method for specific measurement of SOD activity. It is sensitive, rapid and easy to carry out, and it is, moreover, entirely capable of automation; it is therefore suitable for the treatment of large series of samples as may be the case in clinical chemistry.

Moreover, the interferences which are linked to the presence of mercaptans and are frequently encountered in biological samples can easily be removed by the use of at least one "mercaptan-scavenging reagent" as defined above, without another supplementary phase of treatment of the sample.

Finally, the operating conditions of this assay process, which are of high modulability, impart to the process a flexibility in use which enables it to be adapted to very diverse samples, especially biological samples, and therefore to take account of the particular possible requirements of certain users, as is the case in research.

Application examples of the new process for the assay of SOD activity, using seven compounds of general formula I, in the case of an erythrocyte lysate, are given in an illustrative capacity in the experimental section which follows.

The invention also relates to a kit for the implementation of the process for assaying SOD activity according to the invention.

This kit essentially comprises, as reagent, a compound of general formula I as defined above.

According to an advantageous embodiment, the kit for the implementation of the process for assaying SOD activity according to the invention additionally comprises one or more mercaptan-scavenging compound(s) of general formula II as defined above.

According to a preferred embodiment, the invention also relates to a kit for the implementation of the process for assaying SOD activity according to the invention, characterized in that it essentially comprises:

a compound of general formula I in acidic solution or in a powder, one or more mercaptan-scavenging compound(s) of general formula II, in solution or as a powder, and a buffer based on AMPD, which buffers in the pH range from 8.0 to 9.0.

The invention also relates to the compounds of general formula I as defined above, with the proviso that, when $n=1$ and $R^2=CH_2-O-$, $R^1$ and $R^3$ may not simultaneously represent $-OR^4$ where $R^4$=hydrogen.

The attached figures represent calibration curves for the implementation of the process according to the invention, using six different compounds of general formula I, according to the mode of operation which is described, respectively, in Examples 14 to 19 and 21 of the experimental section which follows.

These calibration curves were obtained according to two different methods which are given here by way of example, namely:

First method:

curveting the inverse of the "SOD concentration", expressed in ml/U (U=unit of SOD activity) on the abscissa and curveting the inverse of $V_s-V_c$, $V_s$ and $V_c$ being as defined above, expressed in min/ΔAbs. (ΔAbs.=change in absorbance) on the ordinate.

Second method:

curveting the "SOD concentration", expressed in U/ml (U=unit of SOD activity), on the abscissa and curveting the ratio $V_s/V_c$, $V_s$ and $V_c$ being as defined above, on the ordinate.

EXPERIMENTAL SECTION

Figure 1:
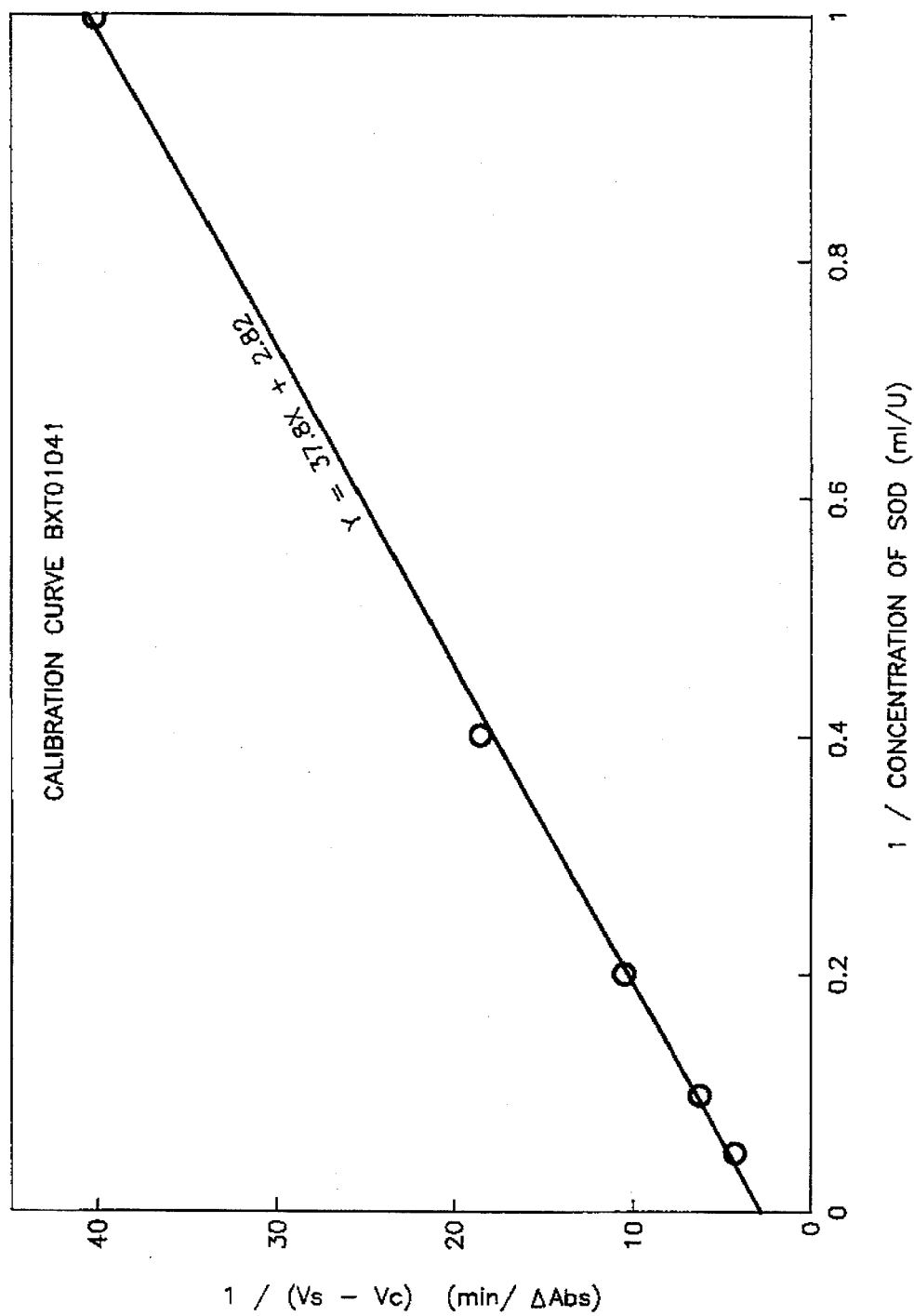
FIG. 1 represents the calibration curve of the compound BXT01041, obtained according to the first method.

I. Preparation of Compounds of General Formula I

All of the reactions were carried out under an inert nitrogen atmosphere unless otherwise indicated.

The mass spectra (MS) were recorded on an R10-10B apparatus from the company Nermag. The ionization mode used is either electron impact (EI) at 70 electron-volts or chemical ionization (CI), unless otherwise indicated.

The $^1$H NMR spectra were recorded on a Gemini-200 type apparatus from the company VARIAN. The chemical shifts are expressed in ppm in relation to tetramethylsilane. The multiplicities are expressed as follows: "s" for singlet; "d" for doublet; "t" for triplet; and "m" for multiplet.

The melting points (m.p.) were recorded with an apparatus from the company Gallenkamp and are given in uncorrected form. The recrystallization solvents are indicated in brackets.

A. Compounds of Series I

EXAMPLE 1

Preparation of 5,6-dihydroxy-1-(4-hydroxyphenyl)indane (BXT01041)

5,6-Dimethoxy-3-(4-methoxyphenyl)indene

A small portion of 4-bromoanisol is added to a suspension of magnesium (0.24 g, 10 mmol) in 5 ml of anhydrous THF. the mixture is heated slightly to initiate the reaction, then the rest of the bromine derivative (1.87 g, 10 mmol) dissolved in 5 ml of THF is added dropwise over the course of 15 min. After refluxing for 1 h, the magnesium has disappeared. The mixture thus obtained is cooled to room temperature, and a solution of 5,6-dimethoxyindan-1-one (1.92 g, 10 mmol) in 10 ml of anhydrous THF is added. The brown solution obtained is stirred for 20 h under these conditions and then hydrolysed by addition of saturated NH$_4$Cl solution. The mixture is extracted with AcOEt. The organic phases collected are washed with saturated aqueous NaCl solution and dried over Na$_2$SO$_4$. After evaporation of the solvent, a yellow oil (3.43 g) is obtained which is taken up in 5 ml of glacial acetic acid. The solution is stirred for 15 min at room temperature and then heated at 70° C. for 15 min. The solution is cooled to 0° C. and poured slowly into 50 ml of saturated NaHCO$_3$ solution. The mixture is extracted with AcOEt. The organic phases collected are washed with saturated aqueous NaHCO$_3$ solution, dried over MgSO$_4$ and evaporated. The crude product (2.84 g) thus obtained is purified by chromatography, eluting with a 1:3 mixture of AcOEt/hexane to give a white solid (1.97 g, 70%).

Physical characteristics:

*m.p.: 111.0°–112.0° C. (AcOEt/hexane=1:3). $^1$H NMR (CDCl$_3$): 3.62 (d, J=2.16 Hz, 2H); 4.05 (s, 3H); 4.08 (s, 3H); 4.12 (s, 3H); 6.58 (t, J=2.16 Hz, 1H); 7.19 (d, J=8.67 Hz, 2H); 7.29 (s, 1H); 7.32 (s, 1H); 7.72 (d, J=8.67 Hz, 2H).

*MS (EI): 282 (100), 267 (55), 251 (19), 181 (24), 165 (35), 152 (51), 84 (53).

5,6-Dimethoxy-1-(4-methoxyphenyl)indane

A solution of 5,6-dimethoxy-3-(4-methoxyphenyl)indene (1.5 g, 5.32 mmol) in 60 ml of ethanol is hydrogenated in an autoclave in the presence of palladium on carbon (10%, 25 mg) under 5 bars of hydrogen for 1.5 h. After filtration of the catalyst, the evaporation of the solvent gives an oil which gradually solidifies (1.5 g, 100%).

Physical characteristics:

*$^1$H NMR (CDCl$_3$): 1.99 (m, 1H); 2.45 (m, 1H); 2.90 (m, 2H); 3.72 (s, 3H); 3.79 (s, 3H); 3.87 (s, 3H); 4.24 (t, J=7.97 Hz, 1H); 6.48 (s, 1H); 6.82 (s, 1H); 6.84 (d, J=8.70 Hz, 2H); 7.50 (d, J=8.70 Hz, 2H). *MS (EI): 284 (100), 269 (26), 253 (59), 241 (17), 177 (21), 165 (35), 152 (28), 155 (28), 84 (25), 77 (26).

5,6-Dihydroxy-1-(4-hydroxyphenyl)indane

A solution of BBr$_3$ in CH$_2$Cl$_2$ (1.0M, 3.1 ml, 3.1 mmol) is added dropwise to a solution of the phenylindane obtained above (500 mg, 0.86 mmol) in 2 ml of CH$_2$Cl$_2$, cooled to −70° C. The red solution obtained is heated to room temperature and stirred for 0.5 h at this temperature. The reaction mixture is poured into a mixture of ice-water and AcOEt. The aqueous phase is saturated with NaCl and then extracted twice with AcOEt. The organic phases collected are washed with saturated aqueous NaCl solution, dried over MgSO$_4$ and evaporated to dryness to give a yellow oil (480 mg) which is chromatographed (eluent: AcOEt/hexane=1:1) to give the expected compound (white solid, 400 mg, 93%).

Physical characteristics:

*$^1$H NMR (acetone-d6): 1.90 (m, 1H); 2.41 (m, 1H); 2.79 (m, 2H); 4.08 (t, J=7.97 Hz, 1H); 6.39 (s, 1H); 6.75 (s, 1H); 6.77 (d, J=8.70 Hz, 2H); 6.98 (d, J=8.70 Hz, 2H); 7.77 (s, broad, 3H). *MS (EI): 242 (100), 225 (61).

EXAMPLE 2

Preparation of 5,6-dihydroxy-1-(4-hydroxyphenyl)-2,2-dimethylindane (BXT01045)

5,6-Dimethoxy-2-methylindan-1-one and 5,6-dimethoxy-2,2-dimethylindan-1-one

A mixture of lithium diisopropylamide (LDA, 1.5M in cyclohexane, 7.5 ml, 11.3 mmol) and 15 ml of anhydrous THF is cooled to −78° C. A solution of 5,6-dimethoxyindan-1-one (1.92 g, 10 mmol) in 5 ml of THF is added dropwise thereto. The mixture is stirred for 30 min at −78° C. Methyl iodide (0.93 ml, 15 mmol) is added. After 30 min at −78° C. the solution is heated to room temperature and stirred at this temperature for 4 h. The solution is again cooled to −78° C. and the same quantity of LDA as before is added dropwise. After 30 min, MeI (0.93 ml, 15 mmol) is added. The mixture is stirred for 30 min at −78° C. and then for 4 h at room temperature. The reaction mixture is hydrolysed by the addition of saturated aqueous NH$_4$Cl solution. It is extracted with AcOEt. The organic phases are washed with saturated aqueous NaCl solution, dried over MgSO$_4$ and evaporated to dryness to give a yellow solid (2.23 g). Chromatography, using a 1:9 mixture of AcOEt/hexane as eluent, gives 5,6-dimethoxy- 2,2-dimethylindan-1-one (1.35 g, 61%) and 5,6-dimethoxy- 2-methylindan-1-one (0.43 g, 21%).

Physical characteristics of 5,6-dimethoxy-2,2-dimethylindan- 1-one:

*$^1$H NMR (CDCl$_3$): 1.64 (s, 6H); 2.85 (s, 2H); 3.85 (s, 3H); 3.91 (s, 3H); 6.80 (s, 1H); 7.12 (s, 1H). *m.p.: 134.0°–134.5° C. (EtOH).

Physical characteristics of 5,6-dimethoxy-2-methylindan-1-one:

*$^1$H NMR (CDCl$_3$): 1.22 (d, J=7.41 Hz, 3H); 2.63 (m, 2H); 3.23 (dd, J=9.24–16.85 Hz, 1H); 3.84 (s, 3H); 3.90 (s, 3H); 6.81 (s, 1H); 7.11 (s, 1H). *m.p.: 106.0°–106.5° C. (EtOH).

1-Hydroxy-5,6-dimethoxy-1-(4-methoxyphenyl)-2,2-dimethylindane

A small portion of 4-bromoanisole is added to a suspension of magnesium (72 mg, 3 mmol) in 6 ml of anhydrous THF. The mixture is heated at gentle reflux to initiate the reaction, then the remainder of the brominated derivative (0.56 g, 3 mmol), in solution in 5 ml of THF, is added dropwise over the course of 15 min. After reflux for 1 h, the magnesium has been consumed. 5,6-Dimethoxy-2,2-dimethylindan-1-one (0.66 g, 3 mmol) is added in small portions. The solution is stirred for 1 h at room temperature, then heated at reflux for 4 h. 10 ml of saturated aqueous NH$_4$Cl solution are added at 0° C. The mixture is extracted with AcOEt. The organic phases collected are washed with saturated aqueous NaCl solution, dried over MgSO$_4$ and evaporated to give a yellow oil (1.20 g). Purification by chromatography (eluent: AcOEt/hexane=1:5) enables the isolation of the expected product (0.65 g, 66%).

Physical characteristics:

*$^1$H NMR (CDCl$_3$): 0.62 (s, 3H); 1.13 (s, 3H); 2.60 (d, J=15.10 Hz, 1H); 2.86 (d, J=15.10 Hz, 1H); 3.77 (s, 3H); 3.79 (s, 3H); 3.89 (s, 3H); 3.91 (s, 1H); 6.71 (s, 1H); 6.79 (s, 1H); 6.83 (d, J=9.00 Hz, 2H); 7.19 (d, J=9.00 Hz, 2H).

5,6-Dimethoxy-1-(4-methoxyphenyl)-2,2-dimethylindane

Sodium borohydride (1.40 g, 36.7 mmol) and aluminum trichloride (0.82 g, 6.1 mmol) are added to a solution of the preceding product (0.39 g, 1.25 mmol) in 15 ml of anhydrous THF. The mixture is heated at reflux. It immediately turns pink, then red and finally becomes colorless. After 20 h of reflux, the reaction mixture is poured into a mixture of 20 g of ice and 5 ml of HCl (1N). The aqueous phase is saturated with NaCl and extracted with AcOEt. The organic phases are washed with saturated aqueous NaCl solution, dried over MgSO$_4$ and evaporated to dryness to give a colorless oil. Chromatography, eluting with a 1:10 mixture of AcOEt-hexane, gives the expected product (0.39 g, 66%).

Physical characteristics:

*$^1$H NMR (CDCl$_3$): 0.63 (s, 3H); 1.19 (s, 3H); 2.72 (s, 2H); 3.74 (s, 3H); 3.79 (s, 3H); 3.87 (s, 3H); 3.91 (s, 1H); 6.56 (s, 1H); 6.78 (s, 1H); 6.83 (d, J=8.86 Hz, 2H); 6.98 (d, J=8.86 Hz, 2H).

5,6-Dihydroxy-1-(4-hydroxyphenyl)-2,2-dimethylindane

A solution of BBr$_3$ in CH$_2$Cl$_2$ (1.0M, 4.86 ml, 4.86 mmol) is added dropwise to a solution of the derivative obtained above (0.39 g, 1.25 mmol) in 2 ml of CH$_2$Cl$_2$, cooled to −70° C. The red solution obtained is heated to room temperature and stirred for 1 h at this temperature. The reaction mixture is poured into a mixture of ice-water and AcOEt. The aqueous phase is saturated with NaCl and then extracted twice with AcOEt. The organic phases collected are washed with saturated aqueous NaCl solution, dried over MgSO$_4$ and evaporated to dryness to give a slightly red oil (410 mg) which is chromatographed (eluent: AcOEt/hexane=1:1) to give the expected compound (0.29 g, 86%).

Physical characteristics:

*$^1$H NMR (acetone-d6): 0.71 (s, 3H); 1.17 (s, 3H); 2.60 (s, 2H); 3.80 (s, 1H); 6.46 (s, 1H); 6.72 (s, 1H); 6.75 (d, J=8.74 Hz, 2H); 6.89 (d, J=8.74 Hz, 2H). *MS (EI): 270 (87), 227 (100), 107 (16).

EXAMPLE 3

Preparation of 5,6-dihydroxy-1-(4-hydroxyphenyl)-2-methylindane (BXT01048)

5,6-Dimethoxy-3-(4-methoxyphenyl)-2-methylindene

A small portion of 4-bromoanisole is added to a suspension of magnesium (42 mg, 1.750 mmol) in 5 ml of anhydrous THF. The mixture is heated at gentle reflux to initiate the reaction, then the remainder of the brominated derivative (330 mg, 1.75 mmol), in solution in 5 ml of THF, is added dropwise over the course of 15 min. After 1 h of reflux, magnesium has been consumed. The mixture thus obtained is cooled to room temperature and then a solution of 5,6-dimethoxy-2-methylindan-1-one (300 mg, 1.46 mmol) in 5 ml of THF is added. The brown solution obtained is stirred for 18 h, then hydrolyzed by the addition of saturated aqueous NH$_4$Cl solution. The mixture is extracted with AcOEt. The organic phases collected are washed with saturated aqueous NaCl solution, then dried over Na$_2$SO$_4$. After evaporation of the solvent, a yellow oil (0.54 g) is obtained which is taken up in 2 ml of glacial acetic acid. The solution obtained is stirred for 1 h at room temperature. The solution, cooled to 0° C. is poured slowly into 50 ml of saturated NaHCO$_3$ solution. The mixture is extracted with AcOEt. The organic phase is washed with saturated aqueous NaHCO$_3$ solution, dried over MgSO$_4$ and evaporated. The crude product (530 mg) thus obtained is purified by chromatography, eluting with a 1:9 mixture of AcOEt/hexane, to give a colorless oil (0.25 g, 58%).

Physical characteristics:

*$^1$H NMR (CDCl$_3$): 2.09 (s, 3H); 3.35 (s, 2H); 3.82 (s, 3H); 3.86 (s, 3H); 3.89 (s, 3H); 6.78 (s, 1H); 7.00 (d, J=8.70 Hz, 2H); 7.04 (s, 1H); 7.33 (d, J=8.70 Hz, 2H).

5,6-Dimethoxy-1-(4-methoxyphenyl)-2-methylindane

A solution of the above phenylindene (240 mg, 0.81 mmol) in 5 ml of AcOEt is hydrogenated under approximately 10$^6$ Pa (10 atm) of hydrogen in the presence of 20 mg of palladium on carbon (10%) for 2 h. The catalyst is removed by filtration, then the filtrate is evaporated to dryness to give the pure product expected (0.24 g, 99%).

Physical characteristics:

*$^1$H NMR (CDCl$_3$): 0.69 (d, J=6.96 Hz, 3H); 2.58 (dd, J=6.96–14.30 Hz, 1H); 2.80 (m, 1H); 2.96 (dd, J=7.04–14.30 Hz, 1H); 3.75 (s, 3H); 3.77 (s, 3H); 3.88 (s, 3H); 4.25 (d, J=7.68 Hz, 1H); 6.63 (s, 1H); 6.80 (d, J=8.78 Hz, 2H); 6.81 (s, 1H); 6.88 (d, J=8.78 Hz, 2H). *MS (EI): 298 (100), 283 (25), 267 (44), 252 (7), 238 (12), 167 (42), 149 (42), 135 (33), 84 (62).

5,6-Dihydroxy-1-(4-hydroxyphenyl)-2-methylindane

A solution of BBr$_3$ in CH$_2$Cl$_2$ (1.0M, 3.0 ml, 3.0 mmol) is added dropwise to a solution of the phenylindane obtained above (0.23 g, 0.77 mmol) in 2 ml of CH$_2$Cl$_2$, cooled to −70° C. The red solution obtained is heated to room temperature and stirred for 0.5 h at this temperature. The reaction mixture is poured into a mixture of ice-water and AcOEt. The aqueous phase is saturated with NaCl, then extracted twice with AcOEt. The organic phases collected are washed with saturated aqueous NaCl solution, dried over MgSO$_4$ and evaporated to dryness to give a yellow oil (0.20 g) which is chromatographed (eluent: AcOEt/hexane=1:1) to give the expected compound (0.18 g, 91%).
Physical characteristics:
*¹H NMR (acetone-d6): 0.63 (d, J=6.96 Hz, 3H); 2.45 (dd, J=7.32–14.22 Hz, 1H); 2.68 (m, 1H); 2.84 (dd, J=7.04–14.22 Hz, 1H); 4.13 (d, J=7.42 Hz, 1H); 6.50 (s, 1H); 6.73 (m, 5H); 7.53 (s, 1H); 7.55 (s, 1H); 8.06 (s, 1H).
*MS (EI): 256 (100), 241 (23), 239 (46), 227 (27).

EXAMPLE 4

Preparation of 1-(4-dimethylaminophenyl)-5,6-dihydroxyindane (BXT01049)

5,6-Dihydroxyindan-1-one 5,6-Dimethylindan-1-one (3.13 g; 16.3 mmol) is dissolved in 10 ml of dichloromethane dried over 3A sieve. A solution of boron tribromide in dichloromethane (1M; 28 ml, 28 mmol) is added dropwise at −70° C. to this light yellow solution. The reaction medium turns claret. The temperature of the medium is brought to room temperature, then the solution is stirred for 2 h 30. The reaction medium is poured onto 50 g of ice, then extracted with ethyl acetate. The organic phases are washed with saturated aqueous NaCl solution, then dried over MgSO$_4$. The solvent is evaporated under reduced pressure.

The crude product (2.3 g; 87%) is used as it is for the following step.

5,6-Di(tert-butyldimethylsilyloxy)indan-1-one tert-Butyldimethylsilyl chloride (7.35 g; 49.8 mmol) and imidazole (3.82 g; 56.1 mmol) are added to a solution of the 5,6-dihydroxyindan-1-one described above (2 g; 12.2 mmol) in 40 ml of DMF dried over 3A sieve and cooled to 0° C. The temperature is maintained at 0° C. for 10 min, then at room temperature for 16 h. The product is extracted with ethyl acetate. The organic phase is washed with saturated aqueous NaCl solution, then dried over MgSO$_4$. The solvent is evaporated under reduced pressure. The desired product is purified by chromatography with an eluent: 8:2 hexane/ethyl acetate and is obtained in the form of a beige solid (4.5 g; 94%).
Physical characteristics:
*¹H NMR (CDCl$_3$): 0.195 (s, 6H); 0.205 (s, 6H); 0.92 (s, 18H); 2.60 (t, J=7.63 Hz, 2H); 2.95 (t, J=7.63 Hz, 2H); 6.85 (s, 1H); 7.15 (s, 1H).

5,6-Di(tert-butyldimethylsilyloxy)-3-(4-dimethylaminophenyl)indene

Magnesium (124 mg, 5.1 mmol) is covered with 1 ml of distilled THF and heated at 60° C. with stirring. A solution of 4-bromo-N,N-dimethylaniline (1.02 g, 5.1 mmol) in 5 ml of distilled THF is added dropwise over the course of 20 min. The reaction mixture is heated at reflux of the THF for 1 h. A solution of 5,6-di(tert-butyldimethylsilyloxy)indan-1-one (2 g, 5.1 mmol) in 10 ml of distilled THF is added dropwise at room temperature over the course of 5 min to this yellow-green solution. The reaction mixture is brought to reflux for 20 h. The reaction mixture, which is violet in colour, is hydrolyzed by saturated aqueous ammonium chloride solution, then extracted with ethyl acetate. The organic phase is washed with saturated aqueous NaCl solution, then dried over MgSO$_4$. The solvent is evaporated under reduced pressure. The desired product is purified by chromatography with an eluent: 9:1 hexane/ethyl acetate, and is obtained in the form of an oil (0.9 g; 36%)
Physical characteristics:
*¹H NMR (CDCl$_3$): 0.16 (s, 12H); 0.95 (s, 18H); 2.94 (s, 6H); 3.50 (d, J=2.03 Hz, 2H); 6.30 (t, J=2.03 Hz, 1H); 6.75 (m, 2H); 6.95 (s, 1H); 7.08 (s, 1H); 7.45 (d, J=7.85 Hz, 2H).

5,6-Di(tert-butyldimethylsilyloxy)-1-(4-dimethylaminophenyl)indane

A solution of the preceding compound (0.9 g; 1.82 mmol) in 10 ml of methanol and 2 ml of acetone is stirred in the presence of palladium on carbon (10%, 60 mg) at room temperature under a hydrogen pressure of approximately $5 \times 10^5$ Pa (5 bars) for 3 h. The suspension is filtered, then the filtrate is evaporated to dryness under reduced pressure. The desired product is purified by chromatography with an eluent: 9:1 hexane/ ethyl acetate, and is obtained in the form of a light beige solid (0.64 g; 71%).
Physical characteristics:
*¹H NMR (CDCl$_3$): 0.08 (s, 6H); 0.18 (s, 6H); 0.90 (s, 9H); 0.95 (s, 9H); 1.90 (m, 2H); 2.45 (m, 2H); 2.90 (s, 6H); 4.17 (t, J=8.07 Hz, 1H); 6.4 (s, 1H); 6.7 (m, 2H); 7.05 (m, 2H); 7.20 (s, 1H).

5,6-Dihydroxy-1-(4-dimethylaminophenyl)indane

The product obtained previously (0.56 g; 1.12 mmol) is dissolved in 5 ml of distilled THF, then a molar solution of tetrabutylammonium fluoride (2.26 ml; 2.26 mmol) in THF is added with stirring and at room temperature. Stirring is maintained for 1 h at this temperature. After addition of water, the product is extracted with ethyl acetate. The organic phase is washed with saturated aqueous NaCl solution, then dried over MgSO$_4$. The solvent is evaporated under reduced pressure. The desired product is purified by a double chromatography:
1st purification: eluent: 6:4 hexane-ethyl acetate
2nd purification: eluent: 95:5 dichloromethane-methanol.
The desired product is obtained in the form of a mauve oil (190 mg; 62%).
Physical characteristics:
*¹H NMR (CDCl$_3$): 1.96 (m, 2H); 2.44 (m, 2H); 2.89 (s, 6H); 4.1 (t, J=7.2 Hz, 1H); 6.4 (s, 1H); 6.73 (d, J=6.7 Hz, 2H); 6.77 (s, 1H); 7.05 (d, J=6.7 Hz, 2H). *MS (EI): 269 (100), 254 (10), 240 (9), 225 (28), 77 (10).
*HPLC (high performance liquid chromatography): (column: reversed-phase RP18; length: 15 cm; eluent: 94:6 dichloromethane-methanol; flow rate: 1 ml/min, observation wavelength: 254 nm); retention time: 2.37 min; purity: 99.1%.

B. Compounds of Series II

EXAMPLE 5

Preparation of 2,5,6-trihydroxy-1-(4-hydroxyphenyl)indane (BXT01035)

2-Hydroxy-5,6-dimethoxy-1-(4-methoxyphenyl)indane

A solution of BH$_3$ THF (1.0M, 4.26 ml, 4.26 mmol) is added at 0° C. over the course of 15 min to a solution of 5,6-dimethoxy-3-(4-methoxyphenyl)indene (1.0 g, 3.55 mmol) in 10 ml of anhydrous THF. The mixture obtained is stirred for 1 h at the same temperature and then for 4 h at room temperature. The solution is cooled to 0° C. and 3.5 ml of water are added dropwise, then 7 ml of NaOH (10% strength). A saturated aqueous solution of H$_2$O$_2$ (30% strength, 7 ml) is then added and the mixture is stirred for 2 h. The mixture is extracted with 50 ml of AcOEt. The organic phase is washed with 10 ml of water, then dried over MgSO$_4$. Evaporation of the solvent gives a white solid (1.16 g) which is purified by chromatography, eluting with a 1:3 mixture of AcOEt/hexane, to give the expected product (white solid, 0.97 g, 91%).
Physical characteristics:
m.p.: 128.0°–129.0° C. (AcOEt/hexane=1:4). *$^1$H NMR (CDCl$_3$): 1.96 (d, J=4.68 Hz, 1H, exchangeable with D$_2$O); 2.84 (dd, J=6.79–15.39 Hz, 1H); 3.21 (dd, J=6.92–15.39 Hz, 1H); 3.73 (s, 3H); 3.79 (s, 3H); 3.87 (s, 3H); 4.05 (d, J=6.23 Hz, 1H); 4.39 (m, 1H); 6.46 (s, 1H); 6.81 (s, 1H); 6.87 (d, J=8.64 Hz, 2H); 7.07 (d, J=8.64 Hz, 2H). *MS (EI): 300 (100), 282 (18), 257 (27), 239 (5), 165 (7), 121 (15).

2,5,6-Trihydroxy-1-(4-hydroxyphenyl)indane

Aluminum tribromide (2.67 g, 10.0 mmol) is mixed with 24 ml of ethanethiol. The preceding phenylindane (300 mg, 1.0 mmol) is added in a single portion. After 62 h at room temperature, the ethanethiol is evaporated, then the residue is treated with 15 ml of water at 0° C. The mixture is extracted with AcOEt. The organic phases collected are washed with saturated aqueous NaCl solution, dried over Na$_2$SO$_4$ and evaporated to dryness to give a yellow oil (250 mg). Purification by chromatography, using a 1:1 mixture of AcOEt/hexane as eluent, gives the expected product (white solid, 140 mg, 54%).
Physical characteristics:
*$^1$H NMR (acetone-d6): 2.68 (dd, J=6.31–15.02 Hz, 1H); 3.06 (dd, J=6.59–15.30 Hz, 1H); 3.90 (d, J=6.53 Hz, 1H); 4.20 (d, J=5.28 Hz, 1H); 4.29 (m, 1H); 6.30 (s, 1H); 6.68 (s, 1H); 6.76 (d, J=8.47 Hz, 2H); 6.96 (d, J=8.47 Hz, 2H); 7.57 (s, 1H); 7.63 (s, 1H); 8.18 (s, 1H). MS (EI): 258 (100), 240 (40), 229 (13), 215 (39), 183 (27), 165 (32), 107 (46), 77 (28).

EXAMPLE 6

Preparation of 5,6-dihydroxy-1-(4-hydroxyphenyl)-2-methoxyindane (BXT01040)

5,6-Dihydroxy-3-(4-hydroxyphenyl)indene

A solution of BBr$_3$ in CH$_2$Cl$_2$ (1.0M, 9.60 ml, 9.60 mmol) is added dropwise to a solution of 5,6-dimethoxy-3-(4-methoxyphenyl)indene (0.60 g, 2.23 mmol) in 2 ml of CH$_2$Cl$_2$, cooled to −70° C. The red solution obtained is heated at room temperature and stirred for 1 h at this temperature. The reaction mixture is poured into a mixture of ice-water and AcOEt. The aqueous phase is saturated with NaCl then extracted twice with AcOEt. The organic phases collected are washed with saturated aqueous NaCl solution, dried over MgSO$_4$ and evaporated to dryness to give a red solid (0.62 g) which is used directly in the following step.
Physical characteristics:
*$^1$H NMR (acetone-d6): 3.28 (d, J=2.10 Hz, 2H); 6.31 (t, J=2.10 Hz, 1H); 6.88 (d, J=8.45 Hz, 2H); 7.03 (s, 1H); 7.07 (s, 1H); 7.44 (d, J=8.45 Hz, 2H); 7.72 (broad s, 2H); 8.53 (broad s, 1H). *MS (EI): 240 (96), 222 (7), 194 (32), 181 (15), 165 (27), 152 (14), 43 (100).

5,6-Dibenzyloxy-1-(4-benzyloxyphenyl)indene

The crude product from the preceding step (0.62 g) is dissolved in 8 ml of acetone. K$_2$CO$_3$ (1.85 g, 13.38 mmol) and benzyl bromide (1.73 g, 10.0 mmol) are added thereto. The mixture is heated at reflux for 18 h. The solid is filtered off, then the filtrate is evaporated to dryness. The residue is chromatographed directly, eluting with a 1:5 mixture of AcOEt/hexane, to give the expected product (0.82 g) which is used directly in the following step.
Physical characteristics:
*$^1$H NMR (CDCl$_3$): 3.36 (d, J=1.83 Hz, 2H); 5.11 (s, 2H); 5.13 (s, 2H); 5.17 (s, 2H); 6.37 (t, J=1.83 Hz, 1H); 7.01 (d, J=8.72 Hz, 2H); 7.17 (s, 1H); 7.25–7.60 (m, 18H).

5,6-Dibenzyloxy-1-(4-benzyloxyphenyl)-2-hydroxyindane

A solution of BH$_3$.THF (1.0M, 3.20 ml, 3.20 mmol) is added at room temperature over the course of 15 min to a solution of the above phenylindene (0.82 g, 1.61 mmol) in 8 ml of anhydrous THF. The mixture obtained is stirred for 3.5 h at room temperature. The solution is cooled to 0° C. and 3.5 ml of water are added dropwise, then 7 ml of NaOH (10% strength). An aqueous solution of H$_2$O$_2$ (30% strength, 7 ml) is then added and the mixture is stirred for 2 h. The mixture is extracted with AcOEt. The organic phase is washed with water, then dried over MgSO$_4$. Evaporation of the solvent gives a colourless oil (0.95 g) which is purified by chromatography, eluting with a 1:4 mixture of AcOEt/hexane, to give the expected product (white solid, 0.46 g, 54%).
Physical characteristics:
*$^1$H NMR (CDCl$_3$): 2.02 (broad s, exchangeable with D$_2$O, 1H); 2.81 (dd, J=7.00–15.26 Hz, 1H); 3.17 (dd, J=6.64–15.26 Hz, 1H); 4.03 (d, J=6.28 Hz, 1H); 4.34 (m, 1H); 5.01 (s, 2H); 5.06 (s, 2H); 5.15 (s, 2H); 6.57 (s, 1H); 6.86 (s, 1H); 6.92 (d, J=8.72 Hz, 2H); 7.40 (d, J=8.72 Hz, 2H); 7.24–7.50 (m, 15H). MS (CI, NH$_3$): 546 (MNH$_4^+$).

5,6-Dibenzyloxy-1-(4-benzyloxyphenyl)-2-methoxyindane

The preceding alcohol (0.26 g, 0.49 mmol) is mixed with potassium powder (0.11 g, 1.97 mmol). 3 ml of DMSO are added thereto, followed immediately by methyl iodide (0.14 g, 9.85 mmol). The mixture is stirred at room temperature for 3 h. 5 ml of water are added. The mixture is extracted with AcOEt. The organic phases collected are washed with saturated aqueous NaCl solution, dried over MgSO$_4$ and evaporated to give a yellow oil. The purification of this oil by chromatography (eluent: AcOEt/hexane=1:9) gives the expected product (0.26 g, 97%).
Physical characteristics:
*$^1$H NMR (CDCl$_3$): 2.85 (dd, J=7.01–15.35 Hz, 1H); 3.23 (dd, J=6.78–15.35 Hz, 1H); 3.38 (s, 3H); 4.04 (m, 1H); 4.12 (d, J=6.25 Hz, 1H); 5.03 (s, 2H); 5.08 (s, 2H); 5.14 (s, 2H); 6.60 (s, 1H); 6.88 (s, 1H); 6.93 (d, J=8.64 Hz, 2H); 7.10 (d, J=8.64 Hz, 2H); 7.30–7.60 (m, 15H).

5,6-Dihydroxy-1-(4-hydroxyphenyl)-2-methoxyindane

A solution of the preceding compound (0.26 g, 0.48 mmol) in 10 ml of AcOEt is hydrogenated under approximately 10$^5$ Pa (1 atm) of hydrogen in the presence of palladium on carbon (10%, 10 mg). The reaction is finished after 12 h. The catalyst is filtered off, then the solvent is evaporated under reduced pressure to give a yellow oil. This crude product is purified by chromatography (eluent: AcOEt/hexane=1:4) to give the expected product (white solid: 92 mg, 71%).
Physical characteristics:
*$^1$H NMR (acetone-d6): 2.68 (dd, J=6.15–15.62 Hz, 1H); 3.15 (dd, J=6.25–15.62 Hz, 1H); 3.24 (s, 3H); 4.01 (m, 1H); 4.04 (d, J=6.25 Hz, 1H); 6.29 (s, 1H); 6.70 (s, 1H); 6.76 (d, J=8.24 Hz, 2H); 6.98 (d, J=8.24 Hz, 2H), 7.62 (broad s, 2H); 8.17 (broad s, 1H). *MS (EI): 272 (100), 240 (81), 227 (18).

C. Compounds of Series III

EXAMPLE 7

Preparation of 5,6,6a,11b-tetrahydro-3,9,10-trihydroxybenzo[c]fluorene (BXT01050)

2-(3,4-Dimethoxybenzylidene)-6-methoxy-1-tetralone

6-Methoxy-1-tetralone (7.04 g, 40 mmol) and 3,4-dimethoxybenzaldehyde (6.44 g, 40 mmol) are mixed with 100 ml of absolute ethanol. The mixture is stirred for 0.5 h to dissolve as much as possible of the reagents. The introduction of gaseous hydrogen chloride is commenced. An exothermic reaction is noted which enables the complete dissolution of all of the reagents. The round-bottomed flask is cooled from time to time with an ice bath so that the temperature does not exceed 80° C. The mixture is thus saturated with hydrogen chloride after 1 h to give an intense red color. This mixture is allowed to stand at room temperature for 2 h. The reaction mixture is poured into a mixture of 400 ml of water and 40 ml of aqueous NaOH (3N). It is stirred vigorously for 3 h at room temperature. The precipitated solid is filtered over a glass frit, washed with water and finally dried under vacuum, over $P_2O_5$, to give a solid (12.35 g, 95%). A small quantity of product is recrystallized from the mixture AcOEt/hexane=1:2.

Physical characteristics:

*$^1$H NMR ($CDCl_3$): 2.89 (t, J=6.96 Hz, 2H); 3.12 (dt, J=1.70–6.96 Hz, 2H), 3.85 (s, 3H); 3.89 (s, 3H); 3.90 (s, 3H); 6.68 (d, J=2.48 Hz, 1H); 6.85 (dd, J=2.48–8.67 Hz, 1H); 6.88 (d, J=8.14 Hz, 1H); 6.95 (d, J=1.64 Hz, 1H); 7.04 (dd, J=1.64–8.14 Hz, 1H); 7.78 (s, 1H); 8.08 (d, J=8.67 Hz, 1H). *MS (EI): 324 (87), 323 (100), 309 (38), 293 (39), 281 (11). *m.p.: 109.0°–110.0° C. (AcOEt/hexane=1:2).

2-(3,4-Dimethoxybenzyl)-6-methoxy-1-tetralone 2.0 g of palladium on carbon (10%) are added to a solution of the preceding compound (35.0 g, 0.107 mol) in 550 ml of AcOEt. The mixture is hydrogenated under approximately $2\times10^5$ Pa (2 atm) of hydrogen for 1 h. The catalyst is removed by filtration and the filtrate is evaporated to dryness to give 38.4 g of a crude product which is dissolved in 100 ml of hot AcOEt. 130 ml of hexane are added. The crystals formed (23.56 g) are filtered. The filtrate is evaporated to dryness. The residue is chromatographed, eluting with a 1:4 mixture of AcOEt/hexane, to give 6.03 g of the pure product expected.

· Yield: 29.59 g (84%).

Physical characteristics:

*m.p.: 101.0°–102.0° C. (AcOEt/hexane=1:2). *$^1$H NMR ($CDCl_3$): 1.67–1.83 (m, 1H); 2.00–2.14 (m, 1H); 2.51–2.72 (m, 2H); 2.84–2.96 (m, 2H); 3.34–3.48 (m, 1H); 3.82 (s, 3H); 3.84 (s, 3H); 3.85 (s, 3H); 6.64 (d, J=2.36 Hz, 1H); 6.74–6.84 (m, 4H); 8.02 (d, J=8.74 Hz, 1H). MS (EI): 326 (35), 175 (9), 151 (100), 107 (13), 91 (17), 77 (11).

5,6-Dihydro-3,9,10-trimethoxybenzo[c]fluorene 15.0 g of polyphosphoric acid are mixed with the tetralone obtained previously (1.04 g, 3.2 mmol), and are then heated at 80°–90° C. for 4 h. After having cooled the mixture to room temperature, 10 g of ice-water and 20 ml of AcOEt are added. The organic phase is separated and the aqueous phase is extracted with AcOEt. The combined organic phases are washed with saturated aqueous $NaHCO_3$ solution then with NaCl (sat.), dried over $MgSO_4$ and evaporated to dryness to give a solid (0.91 g) which is purified by chromatography, eluting with a 1:6 mixture of AcOEt/hexane. The expected product (0.61 g) and the starting product (0.24 g) are obtained. the yield of this reaction in relation to the product consumed is 81%.

Physical characteristics:

*$^1$H NMR ($CDCl_3$): 2.59 (t, J=7.77 Hz, 2H); 2.89 (t, J=7.77 Hz, 2H); 3.39 (s, 2H); 3.84 (s, 3H); 3.90 (s, 3H); 3.94 (s, 3H); 6.84 (m, 2H); 7.08 (s, 1H); 7.38 (s, 1H); 7.72 (d, J=9.24 Hz, 1H). *m.p.: 146.5°–147.0° C. (AcOEt/hexane=1:4). *MS (EI): 308 (100), 293 (14), 277 (38), 202 (24), 176 (33), 165 (17), 152 (21).

5,6,6a,11b-Tetrahydro-3,9,10-trimethoxybenzo[c]fluorene 0.15 g of palladium on carbon (10%) is added to a solution of the preceding product (0.90 g, 2.92 mmol) in 30 ml of AcOEt. The mixture is hydrogenated under a pressure of approximately $8\times10^5$ Pa (8 atm) of hydrogen for 5 h. The catalyst is removed by filtration and the filtrate is evaporated to dryness to give the pure product expected (0.90 g, 99%).

Physical characteristics:

*m.p.: 77.0°–79.0° C. (AcOEt/hexane=1:4). *$^1$H NMR ($CDCl_3$): 1.45–1.65 (m, 1H); 1.66–1.80 (m, 1H); 2.75 (dd, J=6.96–15.10 Hz, 1H); 2.68–2.87 (m, 3H); 3.15 (dd, J=6.96–15.10 Hz, 1H); 3.79 (s, 3H); 3.80 (s, 3H); 3.84 (s, 3H); 4.21 (d, J=6.68 Hz, 1H); 6.66 (d, J=2.64 Hz, 1H); 6.76 (s, 1H); 6.78 (s, 1H); 6.83 (dd, J=2.64–8.38 Hz, 1H); 7.33 (d, J=8.38 Hz, 1H). MS (EI): 310 (100), 295 (23), 279 (46), 267 (15), 189 (24), 121 (23).

5,6,6a,11b-Tetrahydro-3,9,10-trihydroxybenzo[c]fluorene

A solution of $BBr_3$ in $CH_2Cl_2$ (1.0M, 6.5 ml, 6.5 mmol) is added dropwise to a solution of the compound obtained previously (0.57 g, 1.84 mmol) in 4 ml of $CH_2Cl_2$, cooled to −70° C. The red solution obtained is heated to room temperature and stirred for 0.5 h at this temperature. The reaction mixture is poured into a mixture of ice-water and AcOEt. The aqueous phase is saturated with NaCl, then extracted twice with AcOEt. The organic phases collected are washed with saturated aqueous NaCl solution, dried over $MgSO_4$ and evaporated to dryness to give a yellow oil (0.50 g). Chromatography of 0.28 g of this oil (eluent: AcOEt/hexane=1:1) enables the isolation of the expected compound (0.24 g, 87%).

Physical characteristics:

*$^1$H NMR (acetone-d6): 1.46 (m, 1H); 1.61 (m, 1H); 2.46–2.81 (m, 4H); 3.01 (dd, J=7.00–14.98 Hz, 1H); 4.05 (d, J=6.68 Hz, 1H); 6.54 (d, J=2.54 Hz, 1H); 6.66 (s, 1H); 6.68 (s, 1H); 6.71 (dd, J=2.54–8.34 Hz, 1H); 7.18 (d, J=8.34 Hz, 1H); 7.50 (broad s, 2H); 7.83 (broad s, 1H). *MS (EI): 268 (82), 251 (31), 240 (100), 161 (21), 145 (26), 77 (30).

EXAMPLE 8

Preparation of 5,6,6a,7,8,12b-hexahydro-2,3,10-trihydroxybenzo[c]phenanthrene (BXT01051)

2'-(3,4-Dimethoxyphenyl)tetral-6-methoxy-2-spiro-1'-cyclopropan-1-one 10 ml of DMSO are added to a mixture of trimethylsulphoxonium iodide (4.40 g, 20 mmol) and sodium hydride (80% strength in mineral oil, 0.80 g, 20 mmol). The mixture is stirred at room temperature for 1.5 h. 30 ml of DMSO are added and then, in small portions, the 2-(3,4-dimethoxybenzylidene)-6-methoxy-1-tetralone described previously is added over the course of 15 min. The mixture is stirred for 18 h at room temperature and then hydrolyzed by the addition of 50 ml of saturated aqueous $NH_4Cl$ solution. The mixture is extracted with AcOEt. The organic phases collected are washed with water, dried over $MgSO_4$ and evaporated under reduced pressure to give a colorless oil (7.0 g). Purification of this oil by chromatography, eluting with a 1:4 mixture of AcOEt/hexane, gives the desired product (5.41 g, 85%).

Physical characteristics:

*$^1$H NMR ($CDCl_3$): 1.26 (dd, J=4.24–7.08 Hz, 1H); 1.68 (m, 1H); 1.85 (m, 2H); 2.70 (m, 2H); 2.94 (dd, J=7.08–8.24 Hz, 1H); 3.83 (s, 3H); 3.85 (s, 3H); 3.86 (s, 3H); 6.64 (d, J=2.52 Hz, 1H); 6.77 (m, 3H); 6.82 (dd, J=2.52–8.50 Hz, 1H); 8.00 (d, J=8.72 Hz, 1H). *MS (EI): 338 (100), 323 (12), 200 (20), 176 (19), 151 (73), 91 (29), 77 (51).

2-(3,4-Dimethoxyphenylethyl)-6-methoxy-1-tetralone

A solution of the cyclopropane derivative obtained previously (1.0 g, 2.96 mmol) and para-toluene sulphonic acid (300 mg) in 20 ml of $CH_2Cl_2$ is stirred at room temperature for 5 h. This solution is then washed with saturated aqueous $NaHCO_3$ solution, dried over $MgSO_4$ and evaporated under reduced pressure to give a yellow oil (1.05 g). The purification of this product by chromatography (eluent: AcOEt/hexane=1:4) gives a solid (0.57 g) which is a mixture of the two isomeric alkenes.

0.53 g of this latter mixture is taken up in 15 ml of AcOEt. The solution is hydrogenated in the presence of palladium on carbon (10%, 50 mg) under a pressure of approximately $2 \times 10^5$ Pa (2 bars) of hydrogen for 1 h. The catalyst is filtered and the filtrate is evaporated under reduced pressure to give the expected product (0.53 g, 57%).

Physical characteristics:

*$^1$H NMR ($CDCl_3$): 1.80 (m, 2H); 2.24 (m, 2H); 2.42 (m, 1H), 2.66 (m, 2H); 2.92 (m, 2H); 3.81 (s, 3H); 3.82 (s, 3H); 3.84 (s, 3H); 6.64 (d, J=2.36 Hz, 1H); 6.77 (m, 3H); 6.79 (dd, J=2.36–8.80 Hz, 1H); 7.97 (d, J=8.72 Hz, 1H). *MS (EI): 340 (2.5), 176 (100), 164 (16), 151 (12).

5,6,7,8-Tetrahydro-2,3,10-trimethoxybenzo[c]phenanthrene 8 g of polyphosphoric acid are mixed with the tetralone obtained previously (0.41 g, 1.21 mmol), then heated at 80°–90° C. for 2.5 h. After having cooled the mixture to room temperature, 20 g of ice-water and 20 ml of AcOEt are added. The organic phase is removed after allowing the medium to settle and the aqueous phase is extracted with AcOEt. The combined organic phases are washed with saturated aqueous $NaHCO_3$ solution, then with saturated aqueous NaCl solution, dried over $MgSO_4$ and evaporated to dryness to give a solid (0.38 g) which is purified by chromatography, eluting with a 1:9 mixture of AcOEt/hexane. The expected product (0.19 g; 49%) is obtained.

Physical characteristics:

$^1$H NMR ($CDCl_3$): 2.31 (m, 4H); 2.66 (m, 4H); 3.80 (s, 3H); 3.82 (s, 3H); 3.89 (s, 3H); 6.77 (m, 3H); 7.08 (s, 1H); 7.44 (d, J=8.42 Hz, 1H). MS (EI): 322 (100), 307 (10), 291 (19), 189 (18), 161 (18).

5,6,6a,7,8,12b-Hexahydro-2,3,10-trimethoxybenzo[c]phenanthrene 20 mg of palladium on carbon (10%) are added to a solution of the preceding product (170 mg, 0.50 mmol) in 10 ml of AcOEt. The mixture is hydrogenated under a pressure of approximately $8 \times 10^5$ Pa (8 atm) for 2.5 h. The catalyst is removed by filtration and the filtrate is evaporated to dryness to give an oil. This oil is purified by chromatography, eluting with a 1:9 mixture of AcOEt/hexane, to give the desired product (150 mg, 88%).

Physical characteristics:

*$^1$H NMR ($CDCl_3$): 1.53 (m, 2H); 1.81 (m, 1H); 2.00 (m, 1H); 2.32 (m, 1H); 2.75 (m, 4H); 3.77 (s, 3H); 3.78 (s, 3H); 3.81 (1H, hidden by the OMe's); 3.85 (s, 3H); 6.65 (m, 4H); 6.99 (d, J=9.16 Hz, 1H). MS (EI): 324 (100), 309 (5), 296 (33), 293 (37), 203 (36), 189 (86), 173 (39).

5,6,6a,7,8,12b-Hexahydro-2,3,10-trihydroxybenzo[c]phenanthrene

A solution of $BBr_3$ in $CH_2Cl_2$ (1.0M, 1.5 ml, 1.5 mmol) is added dropwise to a solution of the derivative obtained previously (150 mg, 0.37 mmol) in 1 ml of $CH_2Cl_2$, cooled to −70° C. The red solution obtained is heated to room temperature and stirred for 0.5 h at this temperature. The reaction mixture is poured into a mixture of ice-water and AcOEt. The aqueous phase is saturated with NaCl, then extracted twice with AcOEt. The combined organic phases are washed with saturated aqueous NaCl solution, dried over $MgSO_4$ and evaporated to dryness to give a yellow oil (0.18 g). Chromatography of this oil (eluent: AcOEt/hexane=1:1) enables the isolation of the expected compound (91 mg, 87%).

Physical characteristics:

*$^1$H NMR (acetone-d6): 1.53 (m, 2H); 1.90 (m, 2H); 2.32 (m, 1H); 2.75 (m, 4H); 3.67 (d, J=4.76 Hz, 1H); 6.48 (s, 1H); 6.55 (s, 1H), 6.59 (m, 2H); 6.88 (d, J=8.88 Hz, 1H); 7.51 (broad s, 2H); 7.95 (broad s, 1H). *MS (EI): 282 (100), 265 (16), 254 (53), 175 (26), 161 (36), 115 (31), 91 (22), 77 (24).

D. Compounds of Series IV

EXAMPLE 9

Preparation of 3-O-methylbrazilin

5',6',7-Tri-O-benzylbrazilin:

A solution of brazilin monohydrate (304 mg; 1.0 mmol; ALDRICH) in acetone (2.5 ml) containing benzyl bromide (0.4 ml; 3.36 mmol; JANSSEN) and anhydrous potassium carbonate (1.06 g; 7.68 mmol; OSI), is heated at reflux under an inert atmosphere for 15 h. The reaction mixture is violet in color. A solution of sodium hydroxide (5 ml, 0.5N) is added, and the solution thus obtained is stirred for 1 h at room temperature. The reaction medium is extracted with ethyl acetate (2×10 ml). The organic phases are combined, washed with water (2×5 ml) and dried over $MgSO_4$. The solvent is evaporated under reduced pressure. The desired product is purified by chromatography on a MERCK F254 silica column (eluent=hexane/AcOEt, 3:1). Yield=530 mg (95.3%).

Physical characteristics:

*$^1$H NMR (200 MHz, $CDCl_3$): 2.45 (s, 1H); 2.83 (d, 1H, J=16.0 Hz); 3.18 (d, 1H, J=16.0 Hz); 3.78 (d, 1H, J=11.3 Hz); 4.02 (d, 1H, J=11.3 Hz); 4.09 (s, 1H); 5.04 (s, 2H); 5.09 (s, 2H); 5.11 (s, 2H); 6.55 (d, 1H, J=2.6 Hz); 6.71 (dd, 1H, J=2.6–8.5 Hz); 6.80 (s, 1H); 6.88 (s, 1H); 7.17 (d, 1H, J=8.5 Hz); 7.42 (m, 15H). *MS (EI): (M$^+$)=556 (2), 466 (1), 181 (2), 108 (3), 91 (100).

5',6',7-Tri-O-benzyl-3-O-methylbrazilin:

Potassium powder (210 mg; 3.80 mmol) is introduced under an inert atmosphere at room temperature into a solution of 5',6',7-tri-O-benzylbrazilin (530 mg; 0.95 mmol) in dry DMSO (4 ml). Methyl iodide (0.12 ml; 1.90 mmol) is then added to the reaction medium which is stirred for 30 minutes under these conditions. After addition of water (5 ml), the solution is extracted with ethyl acetate (15 ml). The organic phase is dried over $MgSO_4$. The solvent is evaporated under reduced pressure. The desired product is purified by chromatography on a MERCK F254 silica column (eluent=hexane/AcOEt, 2:1). Yield=510 mg (94%).

The product is recrystallized from a 3:1 mixture of hexane/AcOEt.

Physical characteristics:

*m.p.=99.5°–100.5° C. *$^1$H NMR (200 MHz, $CDCl_3$): 2.70 (d, 1H, J=15.8 Hz); 3.22 (d, 1H, J=15.8 Hz); 3.38 (s, 3H); 3.67 (d, 1H, J=11.9 Hz); 4.20 (s, 1H); 4.26 (d, 1H, J=11.9 Hz), 5.03 (s, 2H); 5.07 (s, 2H); 5.11 (s, 2H); 6.54 (d, 1H, J=2.6 Hz); 6.68 (dd, 1H, J=2.6–8.5 Hz); 6.78 (s, 1H); 6.88 (s, 1H); 7.17 (d, 1H, J=8.5 Hz); 7.42 (m, 15H). *MS (EI): (M$^+$)=570 (45), (M$^+$-91)= 479 (12), 91 (100).

3-O-Methylbrazilin:

A solution of 5',6',7-tri-O-benzyl-3-O-methylbrazilin (160 mg; 0.28mmol) in a 5:2 mixture of AcOEt/MeOH, containing 10% palladium on carbon (20 mg), is purged for 15 minutes by a stream of hydrogen. The suspension is hydrogenated for 5 h at room temperature with stirring. It is subsequently filtered under an inert atmosphere. The solvent is evaporated under reduced pressure. The desired product gradually crystallizes. Yield=81 mg (96%).
Physical characteristics:
*$^1$H NMR (200 MHz, CD$_3$COCD$_3$): 2.68 (d, 1H, J=15.6 Hz); 3.08 (d, 1H, J=15.6 Hz); 3.28 (s, 3H); 3.52 (d, 1H, J=12.1 Hz); 4.03 (s, 1H); 4.24 (d, 1H, J=12.1 Hz); 6.28 (d, 1H, J=2.5 Hz); 6.48 (dd, 1H, J=2.5–8.5 Hz); 6.64 (s, 1H); 6.71 (s, 1H); 7.18 (d, 1H, J=8.5 Hz); 7.79 (s, 1H); 7.85 (s, 1H); 8.43 (s, 1H). *MS (EI): 300 (5), 268 (4), 110 (6), 84 (41), 66 (49).

EXAMPLE 10

Preparation of brazilane (R$^1$=OH; R$^2$=—CH$_2$—O—; R$^3$=H)

5',6',7-Tri-O-benzyl-3-O-phenyloxythionocarbonylbrazilin:

A solution of methyllithium (0.4 ml of a 1.6M solution in cyclohexane, JANSSEN) is added dropwise, under nitrogen and with stirring, to a solution of 5',6',7-tri-O-benzylbrazilin (280 mg, 0.50 mmol) in 3 ml of THF, cooled to −78° C. Stirring is maintained for 10 minutes at this temperature then for 1 hour at room temperature. The reaction mixture is again cooled to −78° C. and phenyl chlorothionocarbonate (0.21 ml, 0.75 mmol, ALDRICH) is added dropwise. The reaction mixture is allowed to return to room temperature and is stirred for 1 hour. Hydrolysis is carried out using ammonium chloride, then the product is extracted with ethyl acetate (2×10 ml). The organic phases are combined, washed with saturated sodium chloride solution (2×10 ml), then dried over MgSO$_4$. The solvent is evaporated under vacuum. The yellow oil thus obtained is chromatographed on a MERCK F254 silica column. The desired product, eluted with a 1:5 mixture of ether/hexane, is obtained with a yield of 83% (280 mg of a colorless solid).
Physical characteristics:
*$^1$H NMR (200 MHz, CDCl$_3$): 3.51 (d, 1H, J=16.50 Hz); 3.71 (d, 1H, J=16.50 Hz); 3.75 (d, 1H, J=12.17 Hz); 4.58 (s, 1H); 5.05 (s, 4H); 5.09 (s, 2H); 5.27 (d, 1H, J=12.17 Hz); 6.57 (d, 1H, J=2.56 Hz); 6.69 (dd, 1H, J=2.56–8.45 Hz); 6.78 (s, 1H); 6.88 (s, 1H); 7.06 (d, 2H, J=7.30 Hz); 7.19 (d, 1H, J=8.45 Hz); 7.24–7.46 (m, 18H). *MS (EI): (M$^+$-PhOC(OH)=S)=538 (3); 447 (1.5); 419 (3); 91 (100); 60 (80).

5',6',7-Tri-O-benzylanhydrobrazilin

A solution of the thionocarbonate derivative previously obtained (100 mg, 0.15 mmol) in 3 ml of dry toluene is heated at reflux for 2 hours. The solvent of the slightly yellowish solution thus obtained is evaporated under vacuum. The residue is purified by chromatography on a MERCK F254 silica column and eluted with a 1:5 mixture of ether/hexane. The desired product is obtained with a yield of 82% (64 mg).
Physical characteristics:
*m.p.=142°–144° C. (ethyl acetate/hexane=1:4). *$^1$H NMR (200 MHz, CDCl$_3$): 3.30 (s, 2H); 5.05 (s, 2H); 5.12 (s, 2H); 5.17 (s, 2H); 5.21 (s, 2H); 6.58 (s, 1H); 6.60 (dd, 1H, J=2.50–8.41 Hz); 7.13 (s, 1H); 7.30–7.50 (m, 17H). *MS (EI): 538 (12), 447 (3), 419 (6), 91 (100).

Brazilane:

A solution of the preceding derivative (92 mg, 0.17 mmol) in 5 ml of ethyl acetate is hydrogenated in the presence of palladium on carbon (10%, 30 mg, ALDRICH) under a pressure of approximately 8×10$^5$ Pa (8 bars) for 3 hours at room temperature. The suspension is filtered and the solvent is evaporated under vacuum. The desired product is obtained after purification by chromatography on a MERCK F254 silica column with an eluent of 1:1 ether/hexane. Yield=69%.
Physical characteristics:
*$^1$H NMR (200 MHz, CD$_3$COCD$_3$): 2.47 (dd, 1H, J=2.38–15.46 Hz); 2.80 (m, 1H); 3.03 (dd, 1H, J=7.32–15.46 Hz); 3.47 (t, 1H, J=10.62 Hz); 4.02 (dd, 1H, J=4.48–10.62 Hz); 4.06 (d, 1H, J=7.34 Hz); 6.25 (d, 1H, J=2.52 Hz); 6.45 (dd, 1H, J=2.52–8.34 Hz); 6.67 (s, 1H); 6.80 (s, 1H); 7.20 (d, 1H, J=8.34 Hz); 7.55 (s, 1H); 7.61 (s, 1H); 8.15 (s, 1H). *MS (EI): 270 (100), 253 (31), 240 (18), 205 (22), 161 (39), 115 (25), 101 (24).

E. Compound of Series V

EXAMPLE 11

Preparation of 7-O-methylbrazilin

5',6'-O-Methylenebrazilin:

A solution of anhydrous potassium fluoride (145 mg, 2.5 mmol, JANSSEN) and brazilin monohydrate (152 mg, 0.5 mmol, ALDRICH) in 1 ml of dimethylformamide is heated and stirred under nitrogen at 120° C. Dibromomethane (39 μl, 0.55 mmol, JANSSEN) is added. After stirring at this temperature for 18 hours, the reaction mixture is cooled to 0° C. and 4 ml of water are added. The mixture is extracted with ethyl acetate (2×5 ml). The organic phases are combined, washed with water and then with saturated aqueous sodium chloride solution and dried over Na$_2$SO$_4$. The solvent is evaporated under vacuum. The desired product is obtained after purification by chromatography on a MERCK F254 silica column (eluent=ethyl acetate/hexane, 1:1). Yield: 42%

The product is recrystallized from a 1:1 mixture of ethyl acetate/hexane.
Physical characteristics:
*m.p.=264.5° C. (decomposition). *$^1$H NMR (200 MHz, DMSO d$_6$): 2.81 (d, 1H, J=16.3 Hz); 2.86 (d, 1H, J=16.3 Hz); 3.64 (d, 1H, J=11.8 Hz); 3.82 (d, 1H, J=11.8 Hz); 3.88 (s, 1H); 5.36 (s, 1H); 5.91 (s, 1H); 5.93 (s, 1H); 6.18 (d, 1H, J=2.4 Hz); 6.40 (dd, 1H, J=2.4–8.2 Hz); 6.74 (s, 1H); 6.87 (s, 1H); 7.22 (d, 1H, J=8.20 Hz); 9.26 (s, 1H). *SM (EI): 298 (100), 280 (62), 279 (79), 241 (28), 149 (58).

7-O-Methyl-5',6'-O-methylenebrazilin:

Potassium carbonate (183 mg, 1.33 mmol, OSI) and methyl iodide (35 μl, 0.53 mmol, LANCASTER) are added to a solution of 5',6'-O-methylenebrazilin (79 mg, 0.27 mmol) in 2 ml of acetone. The mixture is heated at reflux under nitrogen for 24 hours with stirring. Then, after returning to room temperature, the suspension is filtered. The filtrate is evaporated to dryness and the desired product is obtained after purification by chromatography on a MERCK F254 silica column (eluent=ethyl acetate/hexane, 1:4). Yield=65%.
Physical characteristics:
*$^1$H NMR (200 MHz, CDCl$_3$): 2.58 (s, 1H); 2.80 (d, 1H, J=16.45 Hz); 3.17 (d, 1H, J=16.45 Hz); 3.76 (s, 3H); 3.79 (d, 1H, J=11.8 Hz); 4.00 (d, 1H, J=16.45 Hz); 4.04 (s, 1H); 5.86 (m, 2H); 6.48 (d, 1H, J=2.4 Hz); 6.62 (dd, 1H, J=2.4–8.2 Hz); 6.68 (s, 1H); 6.72 (s, 1H); 7.24 (d, 1H, J=8.20 Hz).

7-O-Methylbrazilin:

A solution of boron trichloride (0.25 ml of a 1M solution in methylene chloride, 0.25 mmol) is added dropwise, under nitrogen and with stirring, to a solution of 7-O-methyl-5',6'-O-methylenebrazilin (50 mg, 0.16 mmol) in 2 ml of methylene chloride. The reaction mixture is stirred at room temperature for 20 hours. Absolute methanol (60 μl) is slowly added, then the solvent is evaporated under vacuum. The residue is taken up in ethyl acetate (5 ml) and washed with water. The organic phase is dried over $Na_2SO_4$ and the solvent is evaporated under vacuum. The desired product is obtained after purification by chromatography on a MERCK F254 silica column (eluent=ethyl acetate/hexane, 1:1). Yield =44%.

Physical characteristics:

*$^1$H NMR (200 MHz, $CD_3COCD_3$): 2.80 (d, 1H, J=16.5 Hz); 3.00 (d, 1H, J=16.50 Hz); 3.70 (s and d, 4H); 3.93 (d, 1H, J=11.30 Hz); 3.98 (s, 1H); 4.48 (s, 1H); 6.37 (d, 1H, J=2.4 Hz); 6.56 (dd, 1H, J=2.4–8.30 Hz); 6.63 (s, 1H); 6.77 (s, 1H); 7.26 (d, 1H, J=8.30 Hz); 7.59 (s, 1H); 7.64 (s, 1H). *MS (EI): 300 (100), 282 (59), 281 (63), 243 (45), 176 (13), 165 (10), 141 (20).

II. Preparation of compounds of general formula II ("mercaptan-scavenging reagents")

EXAMPLE 12

Preparation of 1,4,6-trimethyl-2-vinylpyridinium tetrafluoroborate 4,6-Dimethyl-2-vinylpyridine:

Benzoyl chloride (29.12 g; 0.186 mol; JANSSEN) in 100 ml of THF is added to a solution of 2,4-dimethylpydirine (20 g; 0.186 mol; LANCASTER) in 200 ml of freshly distilled THF, cooled to −20° C. and under an inert atmosphere. The reaction mixture is stirred at this temperature for 20 minutes. Then vinylmagnesium bromide (186 ml of a 1.0M solution in THF) is added and the solution is stirred at room temperature for 0.5 h. The solvent is evaporated under reduced pressure and the residue is taken up in 300 ml of methyl tert-butyl ether. After washing the reaction medium with saturated $NH_4Cl$ solution, the organic phase is dried over $MgSO_4$ and the desired product is purified by chromatography on a MERCK F254 silica column (eluent=hexane/AcOEt, 9:1). Yield=39.5 g (83%), colorless oil.

The preceding product is taken up in 500 ml of toluene, and p-chloranil (tetrachloro-1,4-benzoquinone) (41.7 g; 0.169 mol) is added, and the mixture is then heated at reflux for 2 h. The reaction medium is concentrated under reduced pressure, then sodium hydroxide solution (260 ml, 2N) is added. The product is extracted with methyl tert-butyl ether (300 ml) and purified by chromatography on a MERCK F254 silica column (eluent=hexane/AcOEt, 9:1). Yield=11.1 g (54.2%), pale yellow oil.

Physical characteristics:

*$^1$H NMR (200 MHz, $CD_3COCD_3$): 2.20 (s, 3H); 2.50 (s, 3H); 5.25–5.45 (dd, 2H, J=11.9–18.7 Hz); 6.60–6.90 (m, 3H). *MS (CI, $NH_3$): $MH^+$=134 (100).

1,4,6-Trimethyl-2-vinylpyridinium tetrafluoroborate:

Trimethyloxonium tetrafluoroborate (0.50 g; $3.76\times10^{-3}$ mol) is added in one portion to a solution of 4,6-dimethyl-2-vinylpyridine (0.61 g; $4.13\times10^{-3}$ mol) in 4.0 ml of methylene chloride under an inert atmosphere. The suspension is left to react for 2 h at 25° C. The suspension is filtered and the product is dried under vacuum. Yield=0.162 g (18%), white crystals.

Physical characteristics:

*$^1$H NMR (200 MHz, $CD_3COCD_3$): 2.60 (s, 3H); 2.85 (s, 3H); 4.20 (s, 3H); 6.00 (d, 1H, J=12.8 Hz); 6.25 (d, 1H, J=19.2 Hz); 7.27 (dd, 1H, J=12.8–19.2 Hz); 7.82 (s, 1H); 7.95 (s, 1H). *MS (EI): ($M^+$) 148 (10); 147 (18); 133 (34); 121 (100); 106 (25); 91 (31); 77 (52); 49 (77).

*Microanalysis: Calculated (%) : C 51.10; H 6.00; N 6.00 Found (%): C 49.80; H 6.08; N 5.96.

EXAMPLE 13

Preparation of 1-methyl-4-vinylquinolinium tetrafluoroborate

4-Vinylquinoline:

A solution of 4-quinolinecarboxaldehyde (5 g; $3.18\times10^{-2}$ mol) in 32 ml of benzene, containing triphenylmethylphosphonium iodide (26 g; $6.36\times10^{-2}$ mol), is added under an inert atmosphere to sodium hydroxide solution (96 ml; 5N). The two-phase system is stirred at 45° C. for 30 minutes. After allowing the phases to separate by settling, the aqueous phase is extracted with ethyl acetate (3×100 ml). The organic phases are combined and washed with 1N HCl solution (2×30 ml), then the aqueous phase is neutralized with $NaHCO_3$ and extracted with methylene chloride (3×100 ml). The organic phase is dried over $MgSO_4$. The desired product is purified by chromatography on a MERCK F254 silica column (eluent=cyclohexane/AcOEt, 8:2). Yield=2.8 g (60%).

Physical characteristics:

$^1$H NMR (200 MHz, $CDCl_3$): 5.60(d, 1H, J=10 Hz); 5.95 (d, 1H, J=14 Hz); 7.30–7.55 (m, 4H); 7.60–7.75 (t, 1H, J=4 Hz); 8.07 (t, 2H, J=6 Hz); 8.85 (d, 1H, J=4 Hz).

1-Methyl-4-vinylquinolinium tetrafluoroborate:

Trimethyloxonium tetrafluoroborate (1.58 g; $10.7\times10^{-3}$ mol) is added in one portion under an inert atmosphere to a solution of 4-vinylquinoline (0.72 g; $4.64\times10^{-3}$ mol) in a 2.5:1 mixture of acetonitrile/acetone. The suspension is left to react for 1 h at 25° C. The solvent is evaporated under reduced pressure, and the residue is taken up in 2-propanol (25 ml) then stirred for 30 minutes at room temperature. After addition of ethyl ether (25 ml), the suspension is filtered. The desired product is dried under vacuum. Yield= 0.93 g (60.4%).

Physical characteristics:

*$^1$H NMR (200 MHz, $CD_3COCD_3$): 4.30 (s, 3H); 6.25 (d, 1H, J=12.5 Hz); 6.65 (d, 1H, J=17.5 Hz); 7.85–8.00 (dd, 1H, J=12.5–17.5 Hz); 8.10 (d, 1H, J=7 Hz); 8.35 (m, 2H); 8.57 (d, 1H, J=10 Hz); 8.72 (d, 1H, J=10 Hz); 9.35 (d, 1H, J=7 Hz). *MS (FAB) glycerol-NOBA: positive ion $M^+$=170 (100) negative ion $M^-$=87 (100).

FAB=fast atom bombardment.

NOBA=meta-nitrobenzyl alcohol.

Microanalysis: Calculated (%): C 56.00; H 4.60; N 5.40 Found (%): C 55.56; H 4.35; N 4.12.

III. Application Examples

The operating procedures described hereinafter are examples of the application of the assay process, using respectively the reagents BXT01041 (described in Example 1), BXT01048 (described in Example 3), BXT01049 (described in Example 4) and BXT01050 (described in Example 7), brazilin (commercial product), brazilane (compound of Example 10) and 3-O-methylbrazilin (compound of Example 9) to measure SOD activity in an erythrocyte lysate.

EXAMPLE 14

Assay procedure using the reagent BXT01041

A case is used which contains the reagents described below. This case of reagents must be stored at a temperature of between 0° and 4° C.

Description of the reagents:

R1: $2\times10^{-3}$M solution of BXT01041 in a 50:50 (v/v) mixture of DMSO/$H_2O$ containing 0.15M boric acid. (To be stored at between 0° and 4° C. during the measurements; stable for at least one month after preparation under the abovementioned storage conditions).

R2 : $5\times10^{-2}$M solution of 1,4,6-trimethyl-2-vinylpyridinium tetrafluoroborate in DMSO containing 25% (w/v) of ethylene glycol. (To be stored at between 0° and 4° C. during the measurements; stable for at least one month after preparation).

E: 62.5/37.5 (v/v) absolute ethanol/chloroform. (To be stored at between 0° and 4° C. for the preparation of the sample).

B: 0.05M AMPD/HCl buffer, pH=8.8, containing 0.1 mM DTPA. (Leave to equilibrate in air at 37° C. before the measurements).

Preparation of the sample:

At least 100 μl of total blood are centrifuged at 4° C. and 3000 rpm for 10 minutes. The supernatant is removed. The erythrocyte pellet is washed with 0.9% sodium chloride solution (cooled to between 0° and 4° C.), then centrifugation is carried out at 4° C. and 3000 rpm for 10 minutes. The supernatant is removed. The erythrocyte pellet is taken up and mixed with 4 times its volume of distilled water, cooled to between 0° and 4° C.

200 μl of the mixture E (cooled to between 0° and 4° C.) are added to 125 μl of this erythrocyte lysate diluted to ⅕ on the one hand, and to 125 μl of distilled water on the other hand. Each of the solutions is mixed thoroughly and is centrifuged at 4° C. and 3000 rmp for 10 minutes. The supernatant thus obtained will be used for the assay, respectively for the sample (with the haemoglobin removed) and for the control.

The supernatants must be stored at between 0° and 4° C. for the measurements.

Assay procedure:

The measurements are carried out at 37° C. in a spectrophotometer whose measurement cells are thermostated.

The reaction mixture corresponding to each assay is prepared at the time of measurement, according to the proportions given in the table below for 1 ml cells.

Each reaction is triggered by the addition of 10 μl of reagent R1. After homogenization of the medium, the change in absorbance is recorded immediately and followed for 1 min 30 s.

The absorbance is measured at 501 nm in cells with a path length of 1 cm, against air.

For each measurement, the reaction medium defined in the table below must be incubated for 1 minute at 37° C. before the addition of the reagent R1.

|  | CONTROL | SAMPLES |
|---|---|---|
| R2 | 20 μl | 20 μl |
| Blank sample (*) | 40 μl | — |
| SAMPLES | — | 40 μl |
| B | 930 μl | 930 μl |

(*): Distilled water which has undergone the same extraction procedure as the erythrocyte lysate.

For each of the measurements, the maximum autoxidation rate, expressed in absorbance units per minute, is determined by evaluating the slope of the plot of absorbance over time (at around time t=30s). This slope corresponds to a phase of autoxidation of the reagent BXT01041 which must be linear.

Expression of results:

Given that $V_c$ and $V_s$ are the rates corresponding, respectively, to the control and to the sample, the SOD activity of the latter is calculated using the equation of the straight calibration curve shown in FIG. 1, which represents the changes in the inverse of difference ($V_s-V_c$), expressed in min/change in absorbance (min/ΔAbs.) as a function of the inverse of the concentration of SOD, expressed in ml/U. This straight curve enables the determination of the value on the abscissa which corresponds to an experimentally measured value on the ordinate.

The inverse of this abscissa is then multiplied by the dilution factor D.

The results are thus expressed in units of SOD activity per ml of sample, such that:

Units of SOD activity=$1/\{0.026\times[1/(V_s-V_c)]-0.075\}\times D$

The unit U of SOD activity defined in this method has the singular advantage of providing an invariable reference, taking into account the absence of relatively unstable reagents of protein or enzyme types such as xanthine oxydase.

The use of this unit is highly recommended, but the user may translate it into a weight value of a purified SOD with which he has previously constructed a calibration curve. An estimation by weight of this kind will be severely affected by the percentage of inactive enzyme present in the preparation.

The results may also be expressed, for example, in U/ml of total blood or in U/mg of erythrocyte proteins.

Notes:

The assay procedure may be checked by assaying the SOD activity of an erythrocyte lysate prepared as described above and stored at −70° C. in the form of aliquots, to serve as control. The SOD activity of such aliquots is stable for at least 6 months at −70° C.

The assay must be carried out on an aliquot which is thawed at the time of use.

EXAMPLE 15

Assay procedure using the reagent BXT01048
Identical to Example 14 except that:

In R1, the reagent BXT01041 is replaced by the reagent BXT01048.

The change in absorbance is monitored at 505 nm.

Figure 2:
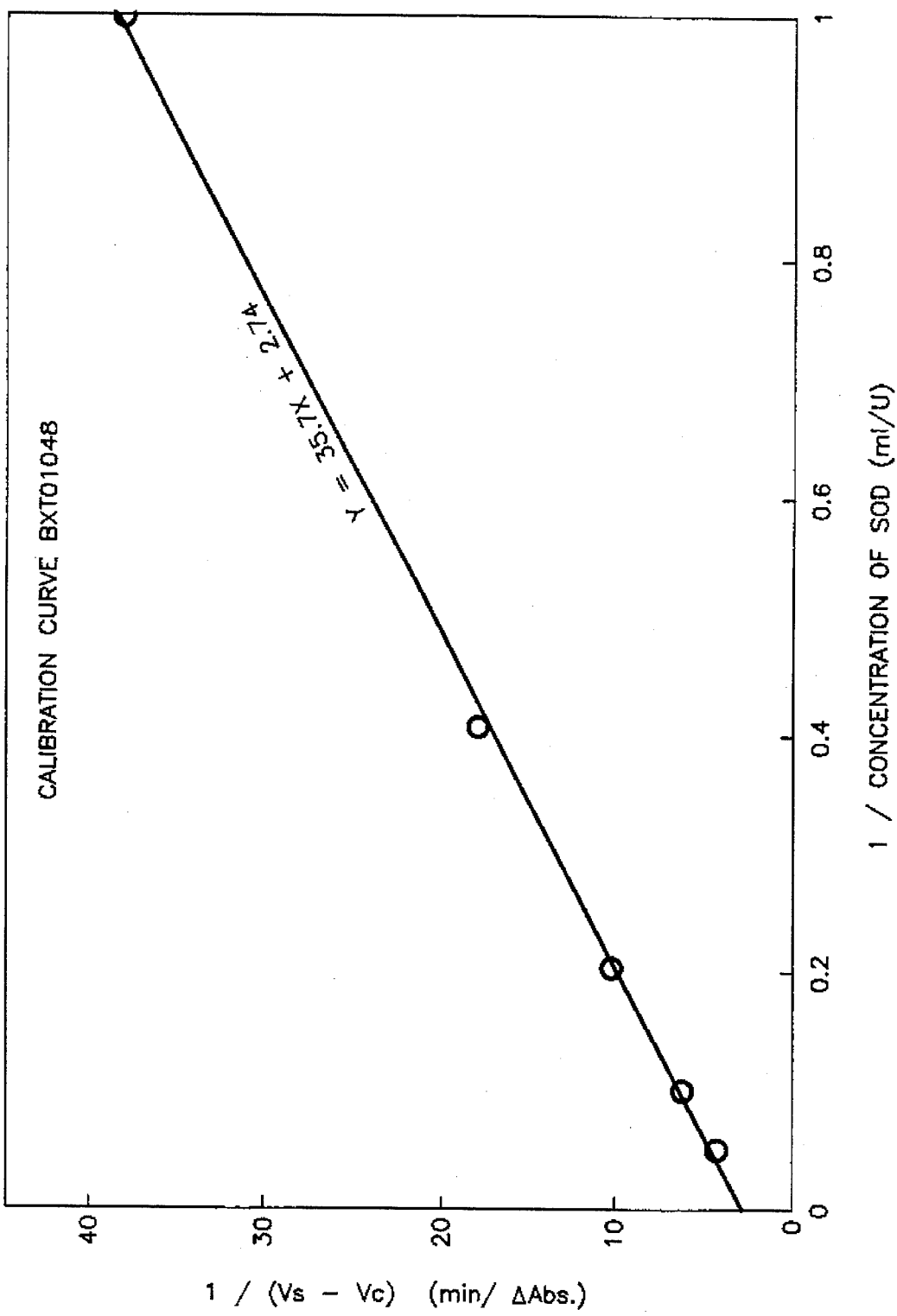
FIG. 2 represents the calibration curve of the compound BXT01048, obtained according to the first method.

FIG. 2 attached shows the changes in the inverse of the difference ($V_s-V_c$), expressed in min/change in absorbance (min/ΔAbs.), as a function of the inverse of the concentration of SOD, expressed in ml/U, in this example.

Units of SOD activity=$1/\{0.028\times[1/(V_s-V_c)]-0.077\}\times D$.

EXAMPLE 16

Assay procedure using the reagent BXT01049
Identical to Example 14 except that:

R1 is replaced by R3 which is defined as follows:

$2\times10^{-3}$M solution of BXT01049 in a 50/50 (v/v) mixture of DMSO/$H_2O$, containing 0.1M boric acid.

The change in absorbance is monitored at 522 nm for 1 min.

Figure 3:
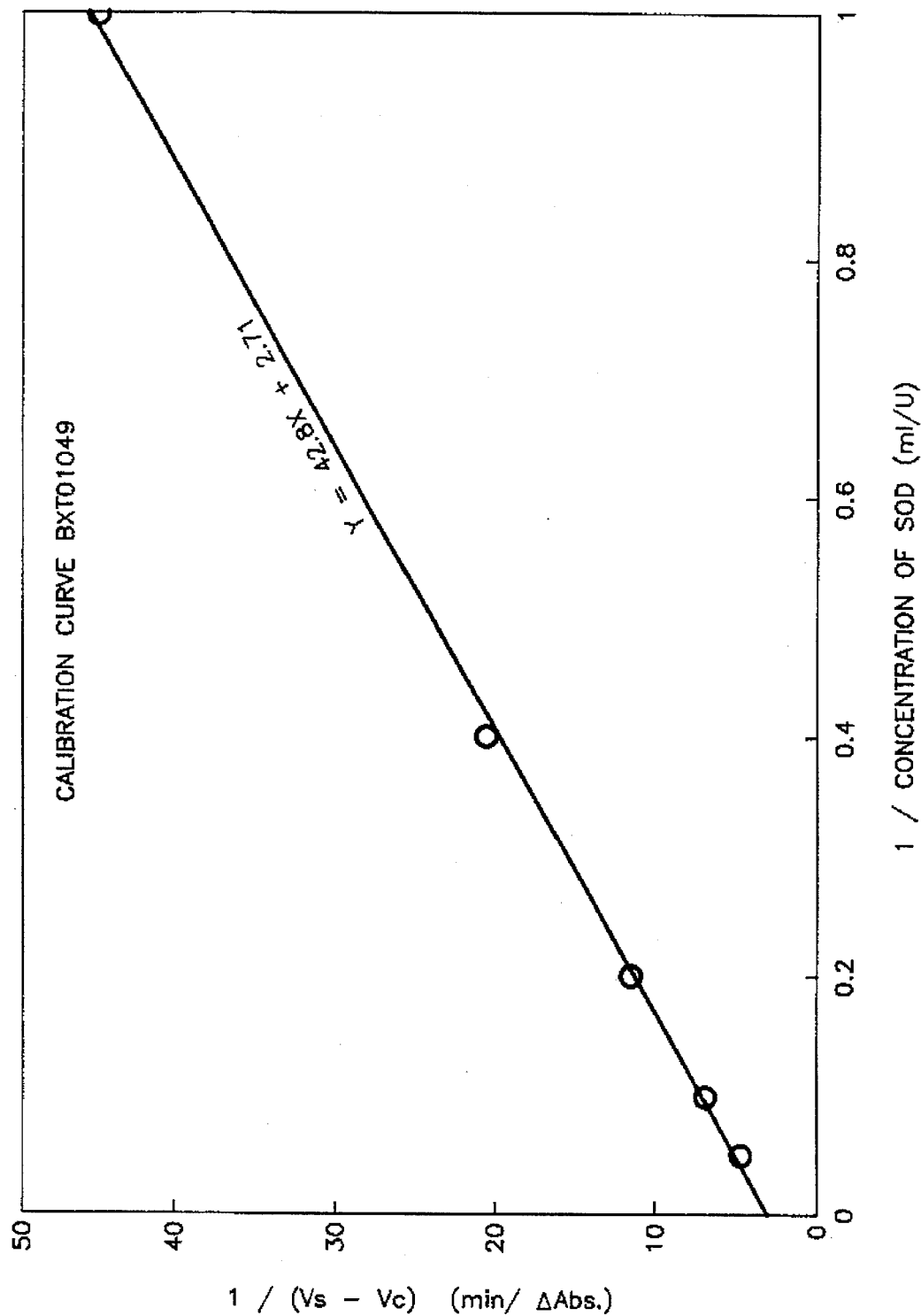
FIG. 3 represents the calibration curve of the compound BXT01049, obtained according to the first method.

FIG. 3 attached shows the changes in the inverse of the difference ($V_s-V_c$), expressed in min/change in absorbance (min/ΔAbs.) as a function of the inverse of the concentration of SOD, expressed in ml/U, in this example.

Units of SOD activity=$1/\{0.023\times[1/(V_s-V_c)]-0.063\}\times D$.

EXAMPLE 17

Assay procedure using the reagent BXT01050
Identical to Example 14 except that:

R1 is replaced by R4 which is defined as follows:
$2 \times 10^{-3}$M solution of BXT01050 in a 50/50 (v/v) mixture of DMSO/H$_2$O, containing 0.3M boric acid.

The change in absorbance is monitored at 525 nm for 1 min.

Figure 4:
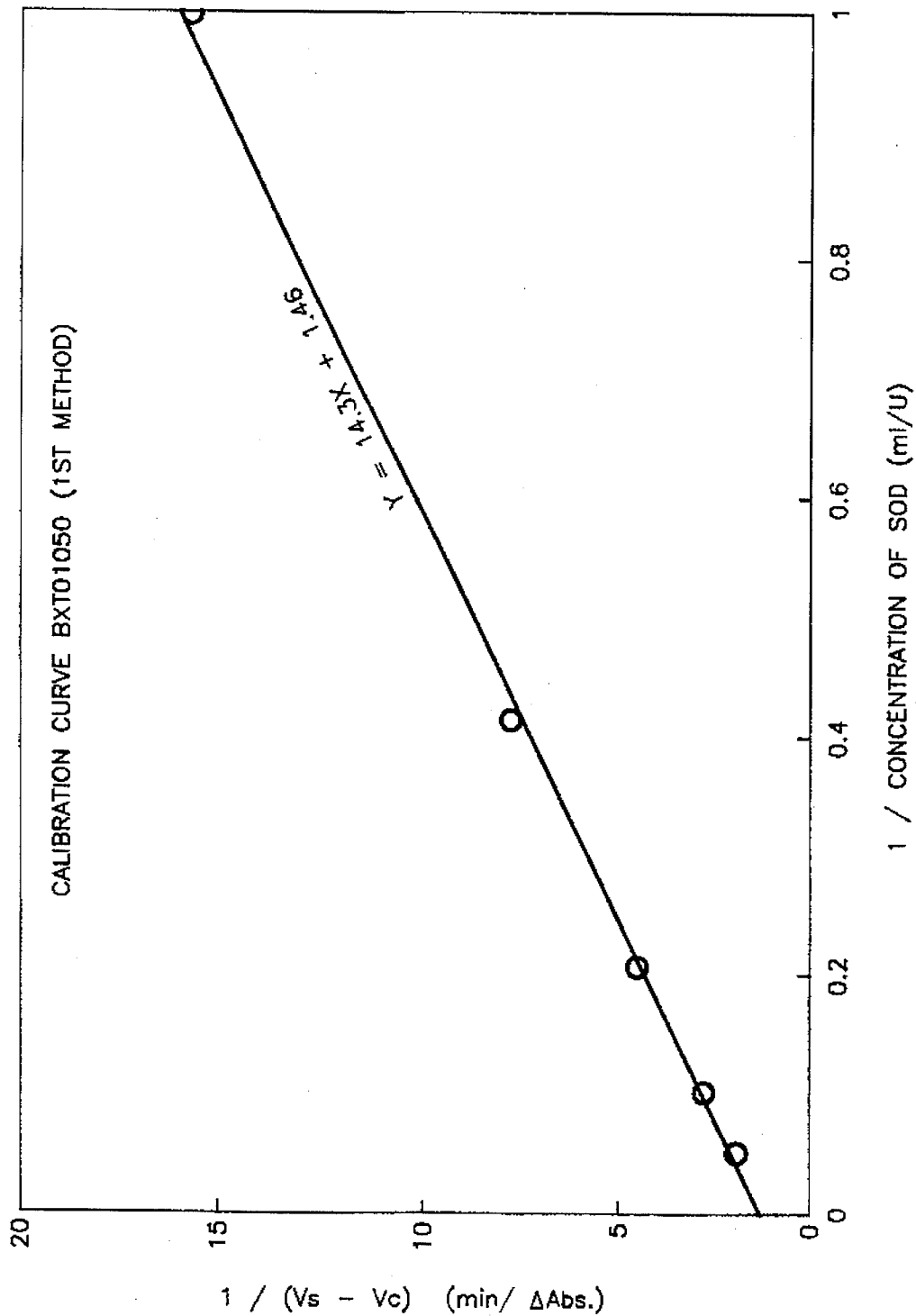
FIG. 4 represents the calibration curve of the compound BXT01050, obtained according to the first method.

FIG. 4 attached shows the variations in the inverse of the difference ($V_s-V_c$), expressed in min/change in absorbance (min/ΔAbs.) as a function of the inverse of the concentration of SOD, expressed in ml/U, in this example.

$$\text{Units of SOD activity} = 1/\{0.070 \times [1/(V_s-V_c)] - 0.102\} \times D.$$

EXAMPLE 18

Assay procedure using brazilin

A box is used which is identical to that used in Example 14 except that in R1 the reagent BXT01041 is replaced by brazilin.

The erythrocyte lysate is obtained as described in Example 14.

200 μl of the mixture E (cooled to between 0° and 4° C.) are added to 125 μl of this erythrocyte lysate diluted to ⅕. The combination is mixed and centrifuged at 4° C. and 3000 rpm for 10 minutes. The supernatant thus obtained, with the haemoglobin removed, will be used for the assay (it must be stored at 4° C. for the measurements).

The assay procedure is the same as in Example 14 except that the absorbance is measured at 539 nm instead of 501 nm and the "blank sample" is replaced by 50% (v/v) ethanol in distilled water.

Expression of results:

Under the conditions of this assay, one unit of SOD activity (U) corresponds to an increase in the formation of brazilein (autoxidation product of brazilin), in relation to the control, of 0.5 μmol.l$^{-1}$. min$^{-1}$.

Figure 5:
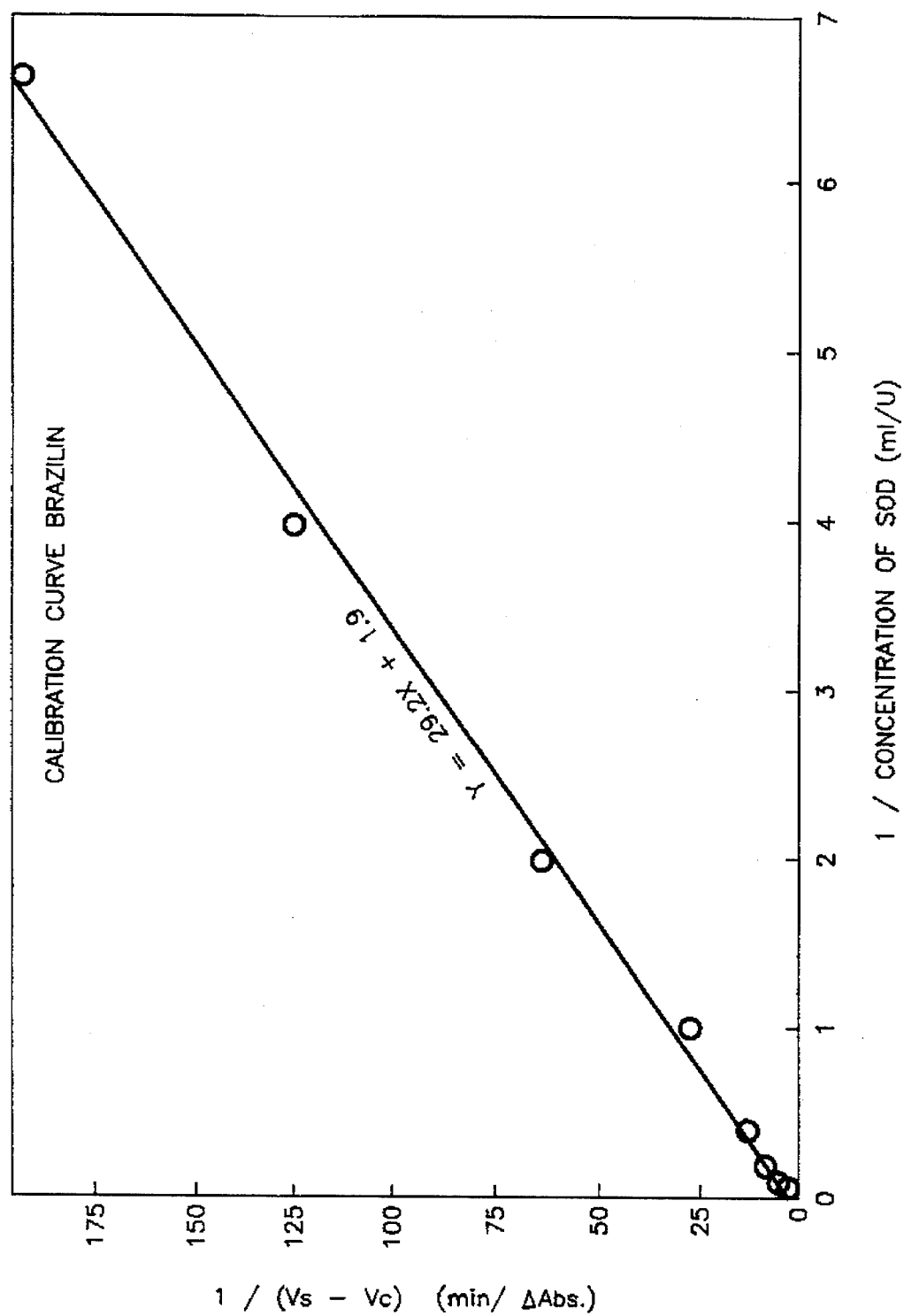
FIG. 5 represents the calibration curve of brazilin, obtained according to the first method.

FIG. 5 attached shows the variations in the inverse of the difference ($V_s-V_c$), expressed in min/change in absorbance (min/ΔAbs.) as a function of the inverse of the concentration of SOD, expressed in ml/U, in this example.

$$\text{Units of SOD activity} = 1/\{0.034 \times [1/(V_s-V_c)] - 0.065\} \times D.$$

EXAMPLE 19

Assay procedure using brazilane

The case of reagents used contains the same reagents as that of Example 14, except that the reagent BXT01041 is replaced by brazilane.

Preparation of the sample:
As in Example 18.

Assay procedure:
The procedure as in Example 18 is followed except that each reaction is triggered by the addition of 10 μl of reagent R1 containing brazilane instead of brazilin, and the change in the absorbance is monitored for 1 min at 520 nm instead of for 1 min 30 s at 539 nm.

Figure 6:
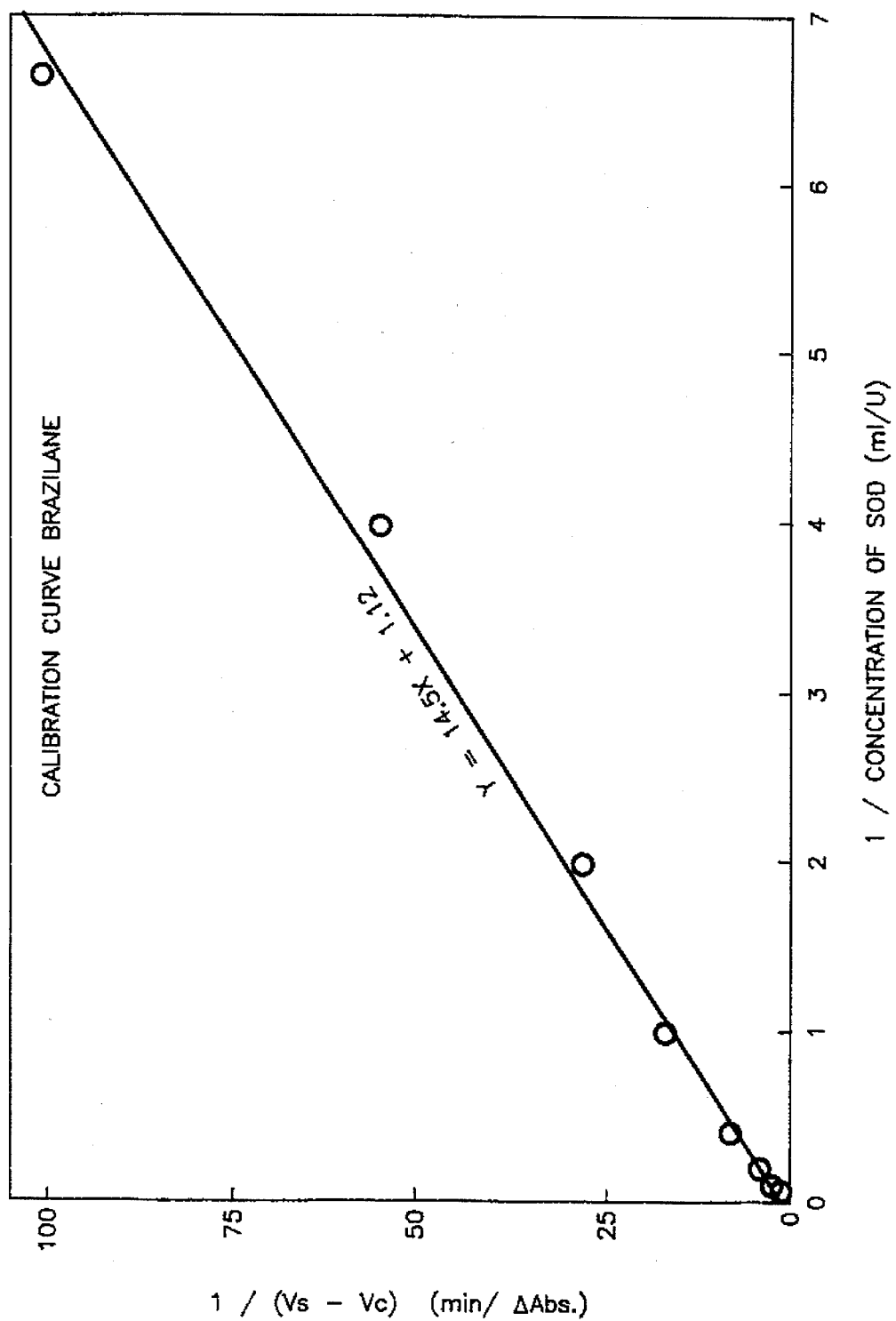
FIG. 6 represents the calibration curve of brazilane, obtained according to the first method.

Expression of results:
FIG. 6 attached shows the variations in the inverse of the difference ($V_s-V_c$), expressed in min/change in absorbance (min/ΔAbs.) as a function of the inverse of the concentration of SOD, expressed in ml/U, in this example.

$$\text{Units of SOD activity} = 1/\{0.069 \times [1/(V_s-V_c)] - 0.077\} \times D.$$

EXAMPLE 20

Assay procedure using 3-O-methylbrazilin

The case of reagents used contains the same reagents as in Example 14 except that the reagent BX01041 is replaced by 3-O-methylbrazilin.

Preparation of the sample:
The preparation of the sample is identical to that described in Example 18.

Assay procedure:
The absorbance is measured at 541 nm. Apart from this the assay procedure is identical to that described in Example 18.

Expression of results:
The expression of the results is identical to that described in Example 18, using a calibration curve specific for 3-O-methylbrazilin.

EXAMPLE 21: Different assay procedure using the reagent BXT01050

A case is used which contains the reagents described below. This case must be stored at a temperature of between 0° and 4° C.

Description of the reagents:

S1: $0.66 \times 10^{-3}$M solution of BXT01050 in $3.2 \times 10^{-2}$M HCl containing 0.5 mM DTPA and 2.5% of absolute ethanol. (To be stored at between 0° and 4° C. for the measurements; stable for at least one month after preparation under the abovementioned storage conditions).

S2: $3.33 \times 10^{-2}$M solution of 1,4,6-trimethyl-2-vinylpyridinium tetrafluoroborate or trifluoromethylsulfonate in DMSO containing 25% (w/v) of ethylene glycol. (To be stored at between 0° and 4° C. during the measurements; stable for at least one month after preparation).

S3: 0.055M AMPD/HCl buffer, pH=8.8 (at 37° C.), containing 3.33 mM boric acid and 0.11 mM DTPA. (Leave to equilibrate in air and at 37° C. before the measurements).

Preparation of the sample:
Identical to Example 14.

Assay procedure:
Identical to Example 17 except that:
Each reaction is triggered by the addition of 30 μl of reagent S1.

The reaction medium is prepared at the time of use in the following way:

|  | CONTROL | SAMPLE |
|---|---|---|
| S2 | 30 μl | 30 μl |
| Blank sample (*) | 40 μl | — |
| SAMPLE | — | 40 μl |
| S3 | 900 μl | 900 μl |

(*): Distilled water which has undergone the same extraction procedure as the erythrocyte lysate.

Expression of results:
The SOD activity of the sample is obtained from the ratio $V_s/V_c$, whose variation with the concentration of SOD (expressed in units of SOD activity) is given by the following equation:

$$V_s/V_c = 1 + [SOD]/(0.073 \times [SOD] + 0.93).$$

Under the conditions of this assay, one unit of SOD activity corresponds to a ratio $V_s/V_c$ of 2 and is called a SOD-525 unit (because the change in the absorbance is monitored at 525 nm, as in Example 17).

Figure 7:
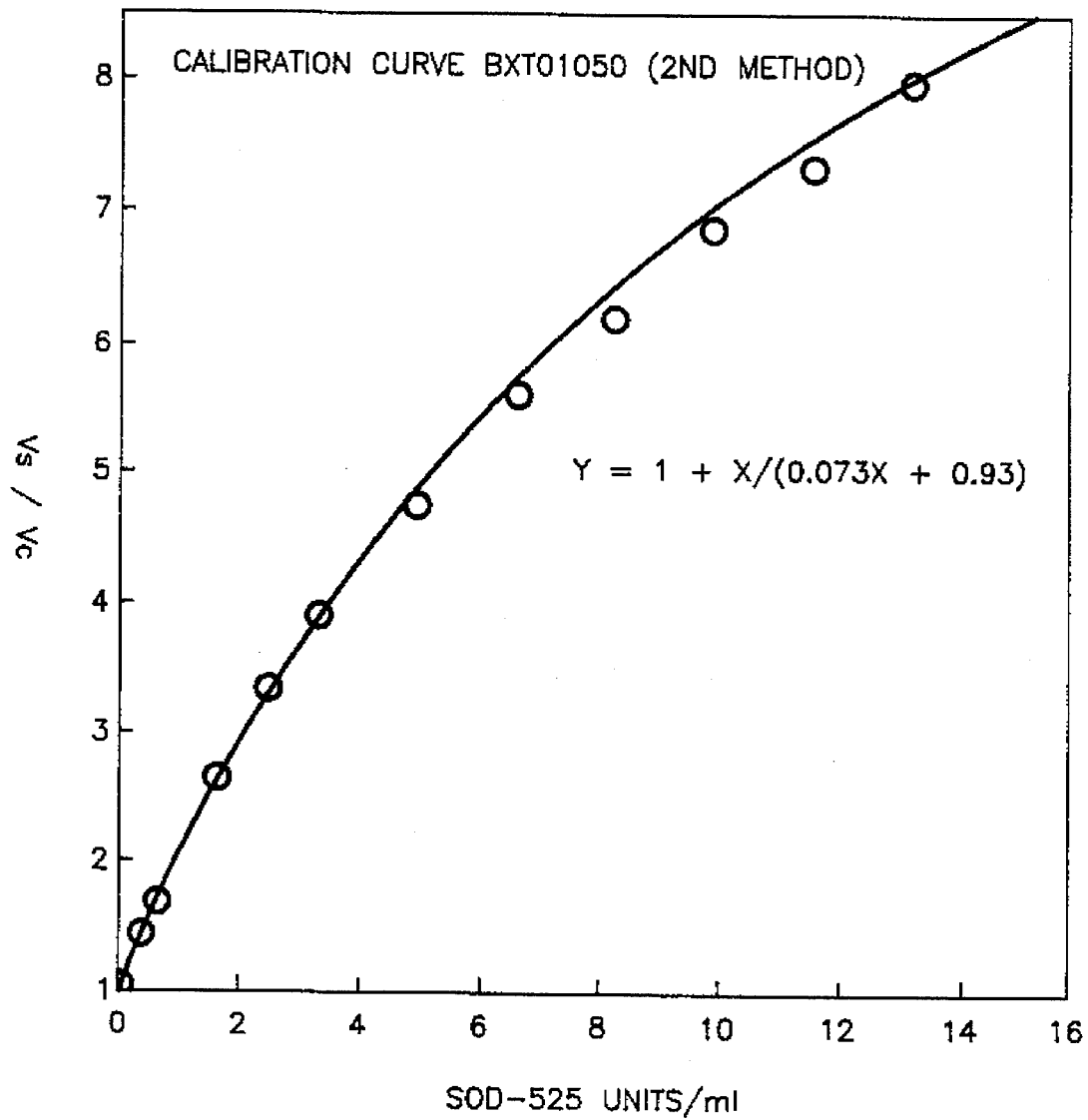
FIG. 7 represents the calibration curve of the compound BXT01050, obtained according to the second method.

FIG. 7 attached shows the variation in the ratio $V_s/V_c$ as a function of the concentration of SOD, expressed in SOD-525 units/ml, in this example.

Units of SOD activity=$[0.93\times(1-V_s/V_c)]/[0.073\times(V_s/V_c-1)-1]\times D$.

REFERENCES

1. FRIDOVICH I. (1986), Biological effects of the superoxide radical; Arch. Biochem. Biophys. 247, 1–11.
2. FRIDOVICH I. (1986a), Superoxide dismutases; Adv. Enzymol. 58, 61–97.
3. FRIDOVICH I. (1989), Superoxide dismutases; an adaptation to a paramagnetic gas; J. Biol. Chem. 264, 7761–7764.
4. KARLSSON K. and MARKLUND S. L. (1988), Extracellular superoxide dismutase in the vascular system of mammals; Biochem. J., 255, 223–228.
5. CZAPSKI G. and GOLDSTEIN S. (1988), The ubiquiness both of superoxide toxicity and of the protective role of superoxide dismutase; in: Oxygen Radicals in Biology and Medicine, SIMIC M. G., TAYLOR K. A., WARD J. F. and VON SONNTAG C. Ed., Plenum Press, New York and London, 43–46.
6. FRIDOVICH I. (1982b), Measuring the activity of superoxide dismutases: an embarrassment of riches; in: Superoxide dismutase Vol. I, OBERLEY L. W. Ed., CRC Press, Boca Raton, Fla., 69–77.
7. FLOHE L. and OTTING F. (1984), Superoxide dismutase assays; Meth. Enzymol., 105, 93–104.
8. BANNISTER J. V. and CALABRESE (1987), Assays for superoxide dismutase; in: Methods of Biochemical Analysis, Vol. 32, John Wiley & Sons, 279–311.
9. FLOHE L., BECKER R., BRIGELIUS R., LENGFELDER E. and OTTING F. (1989), Convenient assays for superoxide dismutase; in: CRC Handbook; Free Radicals and Antioxidants in Biomedicine, Vol. III, MIQUEL J., WEBER H. and QUINTANILHA A. Eds., CRC Press, Boca Raton, Fla., 287–293.
10. GOLDSTEIN S., MICHEL C., BORS W., SARAN M. and CZAPSKI G. (1988), A critical reevaluation of some assay methods for superoxide dismutase activity; Free Rad. Biol. Med., 4, 295–303.
11. MARKLUND S. L. (1976), Spectrophotometric study of spontaneous disproportionation of superoxide anion radical and sensitive direct assay for superoxide dismutase; J. Biol. Chem., 251, 7504–7507.
12. MARKLUND S. L. (1985), Quantitation of superoxide dismutase: Direct assay with potassium superoxide; in: CRC Handbook of Methods for Oxygen Radical Research, GREENWALD R. A. Ed., CRC Press, Boca Raton, Fla., 249–255.
13. MARTIN J. P., DAILEY M. and SUGARMAN E. (1987), Negative and positive assays of superoxide dismutase based on haematoxylin autoxidation; Arch. Biochem. Biophys., 255, 329–336.
14. MARTIN J. P. (1990), Assays for superoxide dismutase based on autoxidation of haematoxylin; Meth. Enzymol., 186, 220–227.
15. TRUCE, KREIDER and BRAND (1971), Org. React., 18, 99–215.
16. COMINS D. L., STROUD E. D. and HERRICK J. J. (1984), Regioselective alkylation of Grignard reagents to the 1-phenoxycarbonyl salts of alkyl nicotinates; Heterocycles, 22 (1), 151–157.

We claim:

1. A process for the assay of superoxide dismutase (SOD) activity in a liquid medium, which uses activation of a reagent by SOD activity comprising the steps of:
   1) adding a compound of general formula I

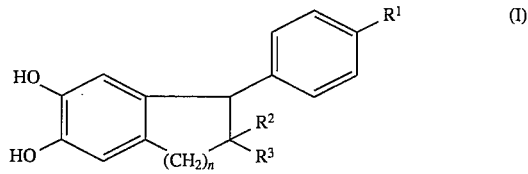

in which:

either:

n=1 or 2, $R^1$=—$OR^4$ or —$NR^5R^6$, $R^2$=hydrogen, —$OR^4$, $C_{1-6}$ alkyl, —$CH_2$ or —$CH_2$—$CH_2$—, to form a ring by linking with the phenyl substituent, in the meta position in relation to $R^1$; and $R^3$=hydrogen, $C_{1-6}$ alkyl or —$OR^4$; with the proviso that $R^2$ is different from —$OR^4$, where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$ alkyl or —$CH_2COOH$;

or:

n=1, $R^1$=—$OR^4$; $R^4$ being defined as above, $R^2$=—$CH_2$—O—, to form a ring by linkage of the oxygen atom with the phenyl substituent, in the meta position in relation to $R^1$, and $R^3$=hydrogen or —$OR^4$; $R^4$ being defined as above, to the medium; and 2) spectrophotometric measurement of the autoxidation rate of said compound of general formula I in the absence and presence of the sample to be assayed.

2. The process for the assay of superoxide dismutase (SOD) activity in a liquid medium containing one or more mercaptans, which process utilizes activation of the autoxidation of a reagent by SOD activity wherein the said reagent of general formula defined in claim 1, further comprising adding a quantity which is capable of totally scavenging the said mercaptans by S-alkylation, of at least one compound conforming to the general formula II:

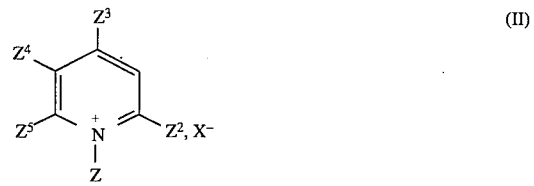

in which:

$Z^1$=$C_{1-6}$ alkyl, benzyl, p-nitrobenzyl, phenyl, o,p-dinitrophenyl, —$CH_2$—COOH or —$CH_2$—$CH_2$—COOH;

$Z^4$=hydrogen and $Z^5$=hydrogen or $C_{1-6}$ alkyl, or $Z^4$ and $Z^5$ form together with the two intermediate carbon atoms; a phenyl ring;

X=halide, sulfonate, fluorosulfonate, phosphonate, tetrafluoroborate or tosylate; and either $Z^2$=vinyl, and $Z^3$=hydrogen or $C_{1-6}$ alkyl, or $Z^3$=vinyl, and $Z^2$=hydrogen or $C_{1-6}$ alkyl, and wherein said process resides in the spectrophotometric measurement of the autoxidation rate of said compound of general formula I in the absence and presence of the sample to be assayed.

3. The process according to claim 2, wherein in said general formula II, X=trifluoromethylsulphonate.

4. A process for the assay of superoxide dismutase (SOD) activity in a liquid sample, comprising the steps of:

1) adding a compound of general formula I

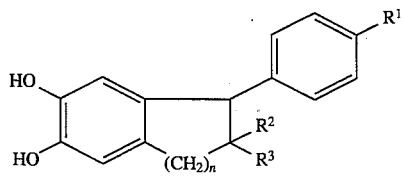

in which:
either:

n=1 or 2, $R^1$=—$OR^4$ or —$NR^5R^6$, $R^2$=hydrogen, —$OR^4$, $C_{1-6}$ alkyl, —$CH_2$ or —$CH_2$—$CH_2$—, to form a ring by linking with the phenyl substituent, in the meta position in relation to $R^1$; and $R^3$=hydrogen, $C_{1-6}$ alkyl or —$OR^4$; provided that $R^2$ is different from —$OR^4$, where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$alkyl or —$CH_2COOH$;

or:

n=1, $R^1$=—$OR^4$ ($R^4$ being defined as above), $R^2$=—$CH_2$—O—, to form a ring by linkage of the oxygen atom with the phenyl substituent, in the meta position in relation to $R^1$; and $R^3$=hydrogen or —$OR^4$; $R^4$ being defined as above; to the sample;

2) contacting the sample with the compound in a reaction medium which is buffered to a pH value of from 8.0 to 9.0, triggering the reaction by the addition of an aliquot of a stock solution of the compound;

3) determining the maximum rate of autoxidation, $V_s$ of the compound in the presence of the sample, by means of the change in the absorbance as a function of time, at the wavelength which characterizes the appearance of the autoxidation product of the compound;

4) determining, under the same conditions, the maximum autoxidation rate, $V_c$ of the same compound in the absence of the sample; and 5) determining under the same conditions, the maximum autoxidation rates for standard samples of known concentration in SOD and plotting a calibration curve setting forth the reverse of the concentration in SOD as the abscissa with respect to the reverse of the difference of the maximum autoxidation rates $1/V_s-V_c$ obtained as the ordinate; and 6) determining the SOD activity by means of the reverse of the difference of the maximum autoxidation rates, $V_s$ and $V_c$ obtained from steps (3) and (4) by using the calibration curve.

5. The process according to claim 1, wherein said process comprises the addition of a boron derivative, to modulate the autoxidation rate of the compound of general formula I.

6. The process according to claim 4, wherein the determination of the maximum rate of autoxidation $V_s$ under the conditions of activation of the autoxidation of the compound of general formula I is combined with the determination of the maximum rate of the autoxidation of the compound of general formula I under conditions in which this autoxidation is inhibited, in a pH range from 7.2 to 7.8.

7. The process according to claim 1, wherein the compound of general formula I is 5,6,6a,11b-tetrahydro-3,9,10-trihydroxybenzo[c]fluorene.

8. Kit for the implementation of the process according to claim 1 which comprises a reagent compound of the general formula I and a container for the reagent.

9. The kit according to claim 8, further comprising one or more mercaptan-scavenging compounds of general formula II.

10. The kit according to claim 9, further comprising:

a compound of general formula I in acidic solution or in a powder, one or more mercaptan-scavenging compounds of general formula II, in solution or as a powder, and a buffer based on AMPD, which buffers in the pH range from 8.0 to 9.0.

11. A compound of general formula I

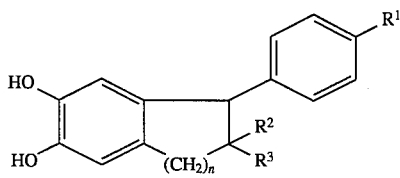

in which:
either:

n=1 or 2, $R^1$=—$OR^4$ or —$NR^5R^6$, $R^2$=hydrogen, —$OR^4$, $C_{1-6}$ alkyl, —$CH_2$ or —$CH_2$—$CH_2$—, to form a ring by linking with the phenyl substituent, in the meta position in relation to $R^1$; and $R^3$=hydrogen, $C_{1-6}$ alkyl or —$OR^4$; provided that $R^2$ is different from —$OR^4$, where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$ alkyl or —$CH_2COOH$;

or:

n=1, $R^1$=—$OR^4$; $R^4$ being defined as above, $R^2$=—$CH_2$—O—, to form a ring by linkage of the oxygen atom with the phenyl substituent, in the meta position in relation to $R^1$; and $R^3$=hydrogen or —$OR^4$; $R^4$ being defined as above; with the proviso that when n=1 and $R^2$=—$CH_2O$—, $R^1$ and $R^3$ may not simultaneously represent —$OR^4$ where $R^4$=hydrogen.

12. A compound of general formula I

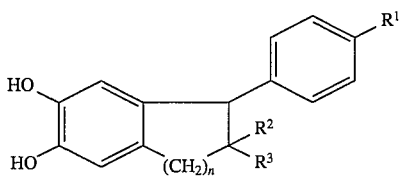

in which:

n=1 or 2;

$R^1$=—$OR^4$ or —$NR^5R^6$, $R^2$=hydrogen, —$OR^4$, $C_{1-6}$ alkyl —$CH_2$ or —$CH_2$—$CH_2$—, to form a ring by linking with the phenyl substituent, in the meta position in relation to $R^1$; and $R^3$=hydrogen, $C_{1-6}$ alkyl or —$OR^4$; with the proviso that $R^2$ is different from —OR4, where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$ alkyl or —$CH_2COOH$.

13. A process for preparing the compound of general formula I

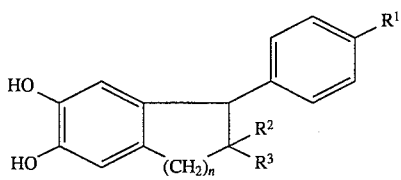

in which:

n=1 or 2;

$R^1$=—$OR^4$ or —$NR^5R^6$, $R^2$=hydrogen, —$OR^4$, $C_{1-6}$ alkyl, —$CH_2$ or —$CH_2$—$CH_2$—, to form a ring by linking with the phenyl substituent, in the meta position in relation to $R^1$; and $R^3$=hydrogen, $C_{1-6}$ alkyl or —$OR^4$; provided that $R^2$ is different from —$OR^4$, where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$ alkyl or —$CH_2COOH$;

or:

n=1, $R^1$=—$OR^4$; $R^4$ being defined as above, $R^2$=—$CH_2$—O—, to form a ring by linkage of the oxygen atom with the phenyl substituent, in the meta position in relation to $R^1$; and $R^3$=hydrogen or —$OR^4$; $R^4$ being defined as above;

in which n=1, $R^4$=OH, $R^2$=$CH_2$—O— and $R^3$=hydrogen, or brazilane, which comprises the steps of:

(1) protecting brazilin on its phenolic hydroxyls, (2) transforming the alcoholic hydroxyl into a group which enables its removal, and (3) reducing, deprotecting and isolating the resulting product.

14. A process for the assay of superoxide dismutase (SOD) activity in a liquid sample, comprising the steps of:

1) adding a compound of general formula I

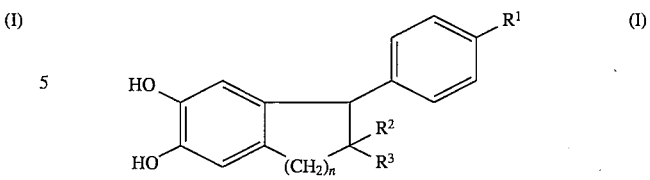

in which:

either:

n=1 or 2, $R^1$=—$OR^4$ or —$NR^5R^6$, $R^2$=hydrogen, —$OR^4$, $C_{1-6}$ alkyl or —$CH_2$—$CH_2$—, to form a ring by linking with the phenyl substituent, in the meta position in relation to $R^1$; and $R^3$=hydrogen, $C_{1-6}$ alkyl or —$OR^4$; provided that $R^2$ is different form —$OR^4$; where $R^4$=hydrogen or $C_{1-6}$ alkyl;

$R^5$=hydrogen, $C_{1-6}$ alkyl, —$CH_2COOH$, —$C_6H_5SO_3H$; and $R^6$=hydrogen, $C_{1-6}$ alkyl or —$CH_2COOH$;

or:

n=1, $R^1$=—$OR^4$; $R^4$ being defined as above, $R^2$=—$CH_2$—O—, to form a ring by linkage of the oxygen atom with the phenyl substituent, in the meta position in relation to R1; and $R^3$=hydrogen or —$OR^4$; $R^4$ being defined as above, to the sample;

2) contacting the sample with the compound in a reaction medium which is buffered to a pH value of from 8.0 to 9.0, triggering the reaction by the addition of an aliquot of a stock solution of the compound;

3) determining the maximum rate of autoxidation, $V_s$ of the compound in the presence of the sample, by means of the change in the absorbance as a function of time, at the wavelength which characterizes the appearance of the autoxidation product of the compound;

4) determining, under the same conditions, the maximum autoxidation rate, $V_c$ of the same compound in the absence of the sample;

5) determining under the same conditions, the maximum autoxidation rates for standard samples of known concentration in SOD and plotting a calibration curve, setting forth the SOD concentration as the abscissa and the ratio of $V_s$ and $V_c$ as the ordinate; and 6) determining the SOD activity of the liquid sample by means of the ratio, $V_s$ and $V_c$ obtained with the liquid sample under steps (3) and (4) by using said calibration curve.

15. The process according to claim 1 wherein the liquid medium is a biological medium from an aerobic organism and human organism.

16. The process according to claim 5 wherein the boron derivative is boric acid.

17. The process according to claim 15 wherein the biological medium is blood.

18. The process according to claim 15 wherein the biological medium is selected from a group consisting of blood plasma, erythrocytes, blood platelets, leucocytes, synovial fluid, cerebrospinal fluid, urine and tissue extract.

* * * * *